(12) United States Patent
Wiessler et al.

(10) Patent No.: US 6,958,395 B2
(45) Date of Patent: Oct. 25, 2005

(54) METHOD FOR PRODUCING WATER-SOLUBLE SACCHARIDE CONJUGATES AND SACCHARIDE MIMETICS BY DIELS-ALDER REACTION

(75) Inventors: Manfred Wiessler, Frankenthal (DE); Hans-Christian Kliem, Heppenheim (DE); Bernd Sauerbrei, Hamburg (DE); Birgit Schmauser, Bonn (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 10/362,961
(22) PCT Filed: Aug. 22, 2001
(86) PCT No.: PCT/DE01/03237
§ 371 (c)(1), (2), (4) Date: Sep. 8, 2003
(87) PCT Pub. No.: WO02/16378
PCT Pub. Date: Feb. 28, 2002

(65) Prior Publication Data
US 2004/0059101 A1 Mar. 25, 2004

(30) Foreign Application Priority Data
Aug. 22, 2000 (DE) .......................................... 100 41 221

(51) Int. Cl.[7] .......................... C07H 21/02; C07H 17/02
(52) U.S. Cl. ...................... 536/124; 536/17.4; 536/119; 536/23.1; 502/150; 530/322; 544/224; 549/427; 568/445; 525/333.6; 512/16; 512/14
(58) Field of Search ................................ 536/17.4, 124, 536/119, 23.1; 502/150; 512/16, 14; 528/322; 508/328; 525/333.6; 526/217; 544/224; 549/427; 568/445; 530/322

(56) References Cited

U.S. PATENT DOCUMENTS 5,169,943 A * 12/1992 Lubineau et al. ............ 536/124
5,705,489 A *  1/1998 Van Boeckel et al. ........ 514/25

FOREIGN PATENT DOCUMENTS

| DE | 39 36 522 | 5/1991 |
| EP | 0 287 353 | 10/1988 |
| EP | 287353 | * 10/1988 |
| EP | 0 505 267 | 9/1992 |
| EP | 0 587 471 | 3/1994 |
| WO | WO 90/12773 | 11/1990 |
| WO | WO 98/47910 | 10/1998 |

OTHER PUBLICATIONS

Helliwell, et al., "Asymmetric synthesis of (5S)04–deoxy–5–C–(4–nitrophenyl)–L–threo–pentose and (5R)–5–C–(4–nitrophenyl)–L–arabinose," *Tetrahedron Letters* 40:8651–8655 (1999).

Jarosz, et al., "Synthesis Of Sugar–Derived 2'–and 3'–Substrituted Furans and Their Application in Diels—Alder Reactions," *Eur. J. Org. Chem.* 2955–2964 (2001).

(Continued)

*Primary Examiner*—James O. Wilson
*Assistant Examiner*—Devesh Khare
(74) *Attorney, Agent, or Firm*—Howrey LLP; Viola T. Kung

(57) ABSTRACT

The present invention relates to a method by which saccharide compounds can be prepared in a very easy way. This method comprises the steps of:
(a) attaching at least one saccharide to a cyclic or acyclic diene,
(b) reacting the saccharide-containing diene obtained in step (a) or a commercially available saccharide-containing diene with a dienophile by Diels-Alder reaction.

Figure 1:
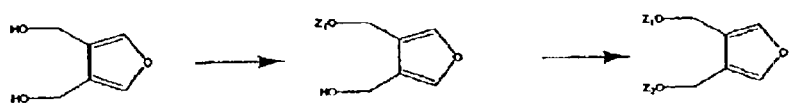

23 Claims, 12 Drawing Sheets $Z_1$ = saccharide 1
$Z_2$ = saccharide 2

OTHER PUBLICATIONS

Lubineau, et al., "Aqueous Cycloadditions Using Glycoorganic Substrates," *ACS Symposium Series*, Chapter 10, pp. 494–156 (1992).

Lubineau, et al., "Preparation of α– and β–dienyl glycosides used as dienes in aqueous Diels–Alder reactions. Influence of the carbohydrated moiety on the thermodynamics of the reaction," *Carbohydrate Research* 270:163–179 (1995).

Pellegrinet, et al., "Diels–Alder Reactions of D–Glucose–Derived Dienophiles with Cyclophentadiene: A Computational Study," *Tetrahedron* 56:5311–5316 (2000).

Pontén and Magnusson, "Synthesis of Polycyclic Oxanorbornanes via a Sequential Epoxyhexopyranoside Ring Contraction–Intramolecular Diels–Alder Reaction," *J. Org. Chem.* 62:7978–7983 (1997).

Trotter, et al., "A Diels–Alder strategy to 1,4–glycosidically linked monocarba–disaccharides," *Tetrahedron Letters* 41:8957–8962 (2000).

\* cited by examiner $Z_1$ = saccharide 1
$Z_2$ = saccharide 2 a)

$Z_1$ = saccharide 1, active substance, nucleic acid, etc.
$Z_2$ = saccharide 2, active substance, nucleic acid, etc.
$Z_3$ = saccharide 3, active substance, nucleic acid, etc.

b)

Fig. 5(a) Preparation of furan derivatives which can be conjugated with saccharides
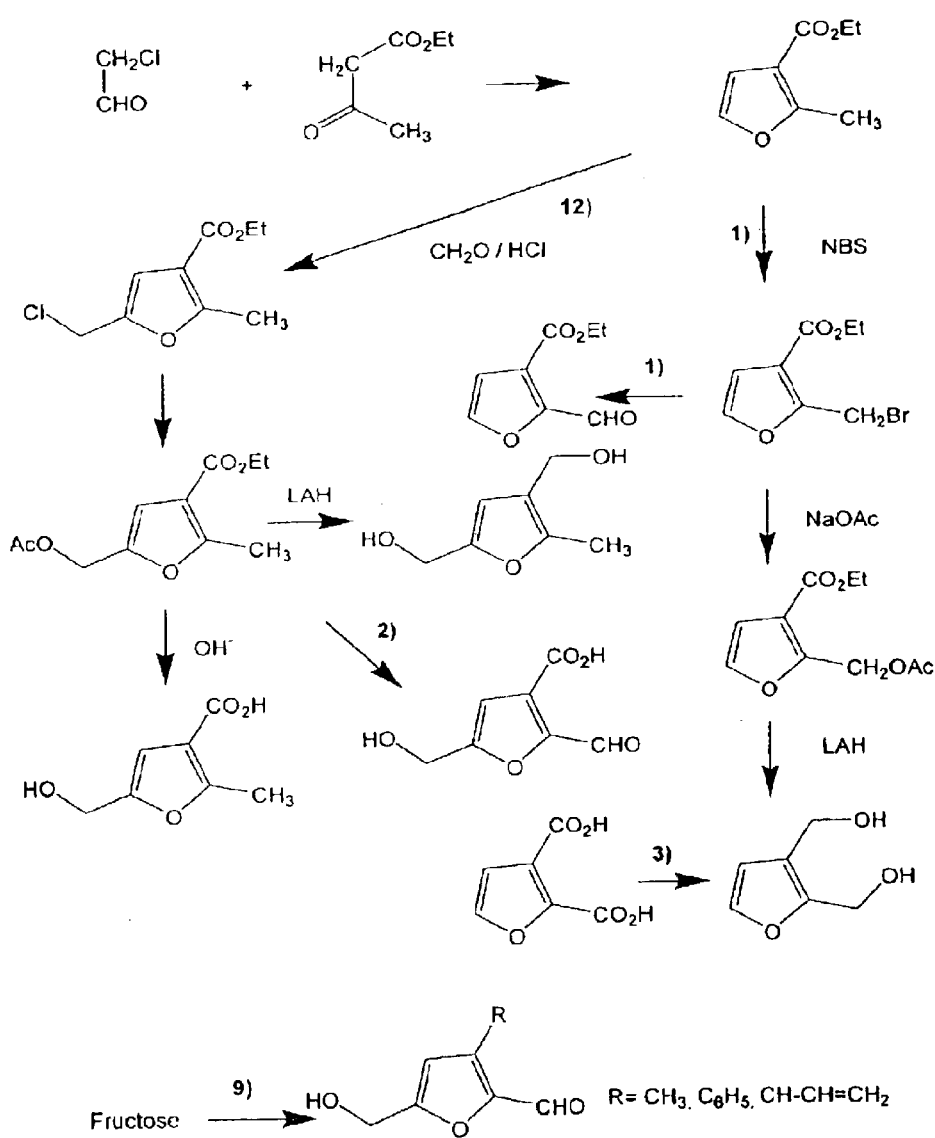

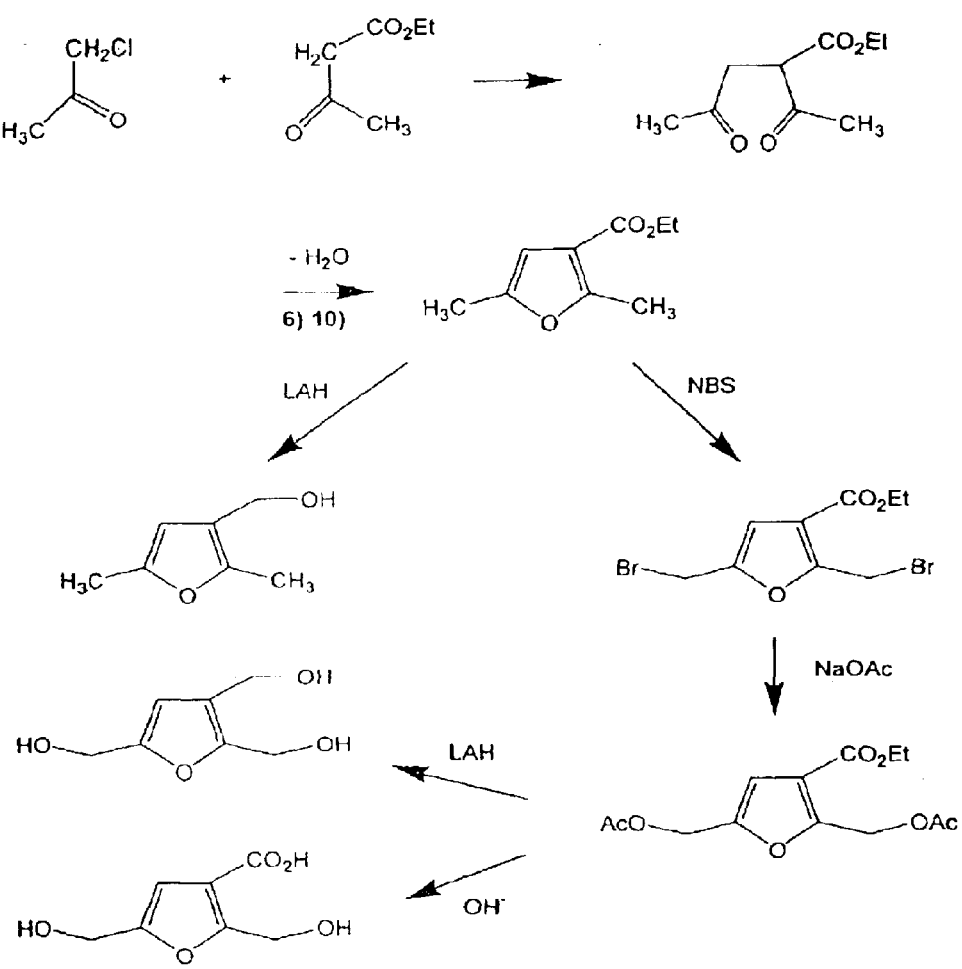
Fig. 5(b) Preparation of furan derivatives which can be conjugated with saccharides

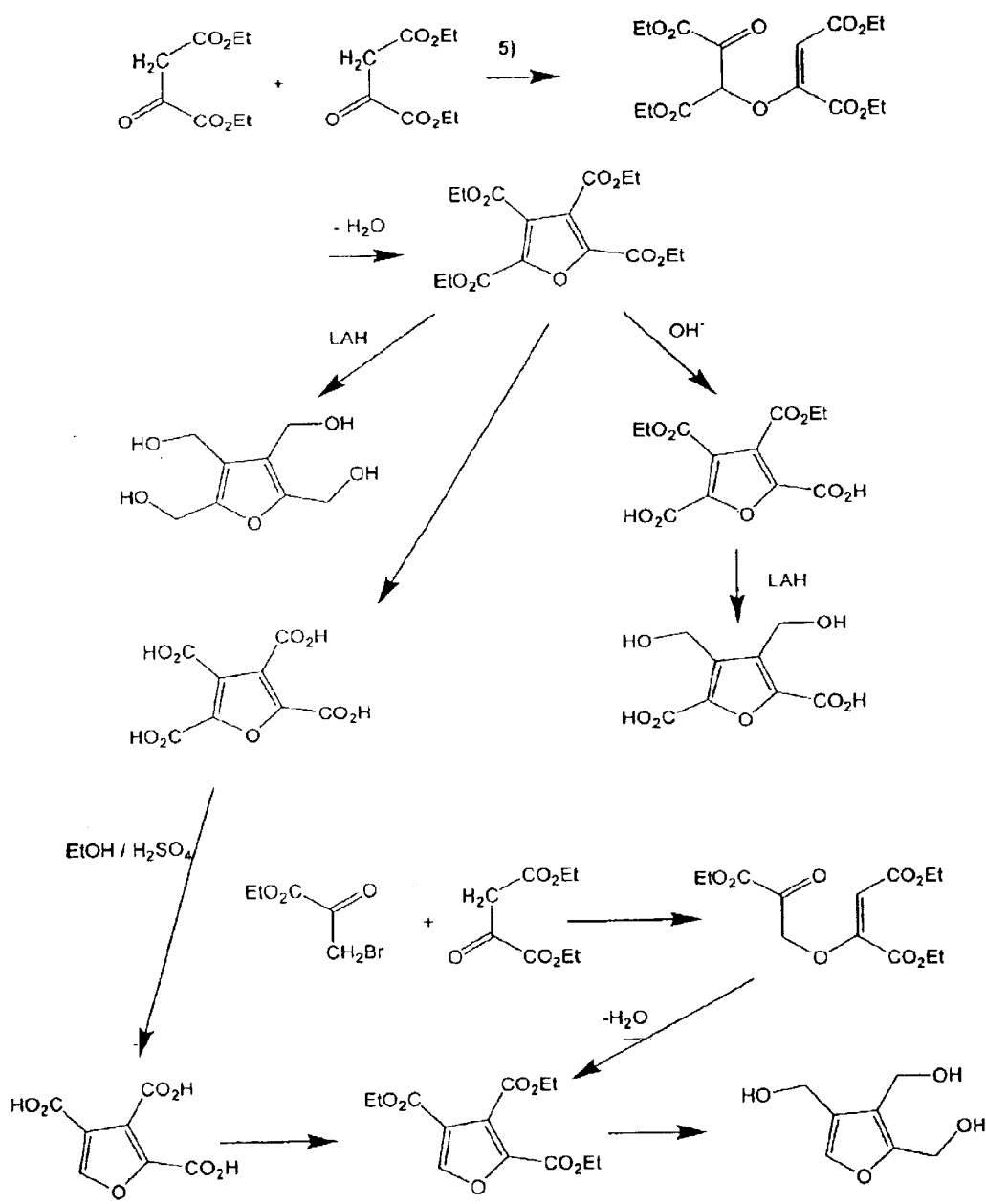
Fig. 5(c) Preparation of furan derivatives which can be conjugated with saccharides Fig. 5(d) Preparation of furan derivatives which can be conjugated with saccharides
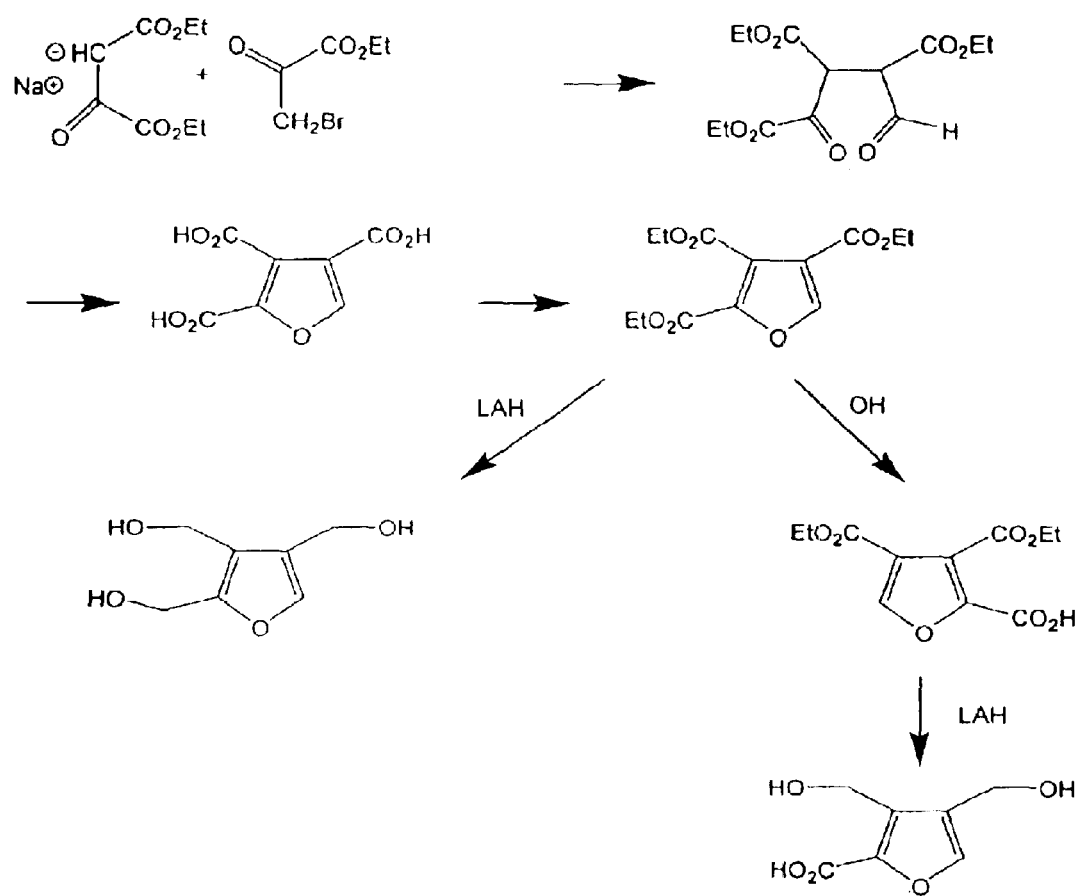

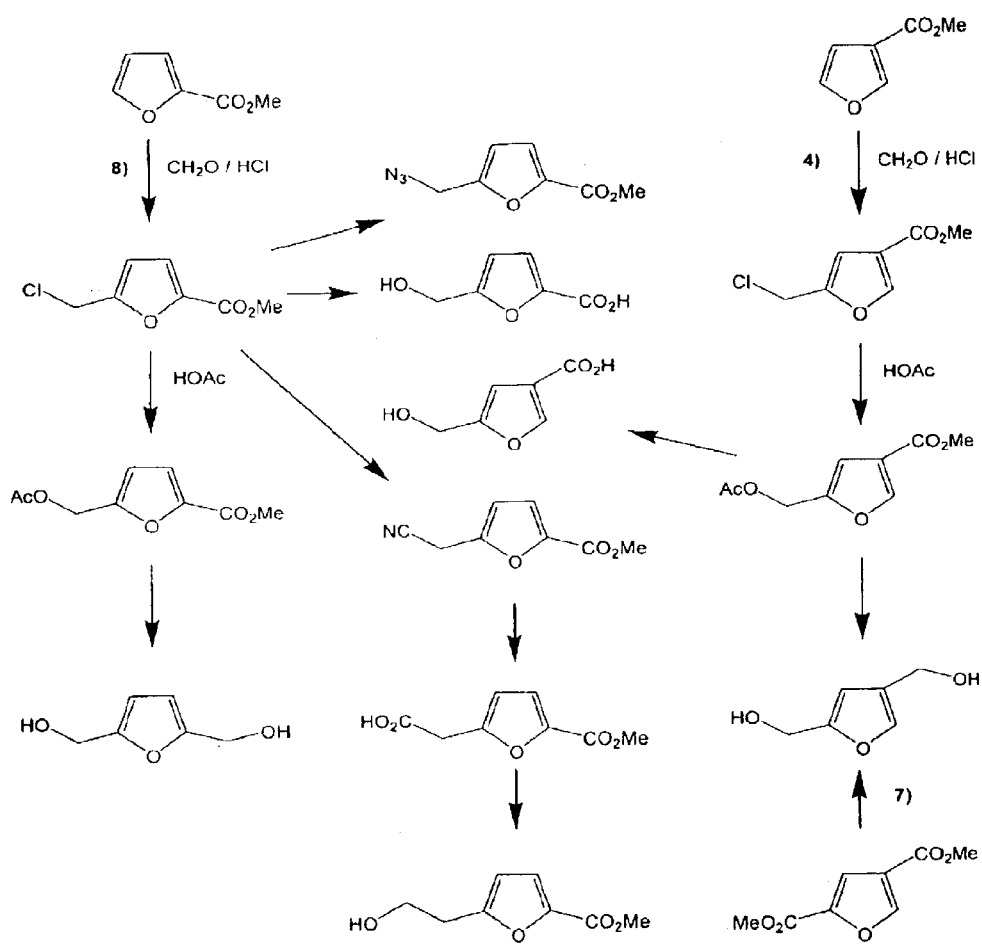
Fig. 5(e) Preparation of furan derivatives which can be conjugated with saccharides Fig. 5(f) Preparation of furan derivatives which can be conjugated with saccharides
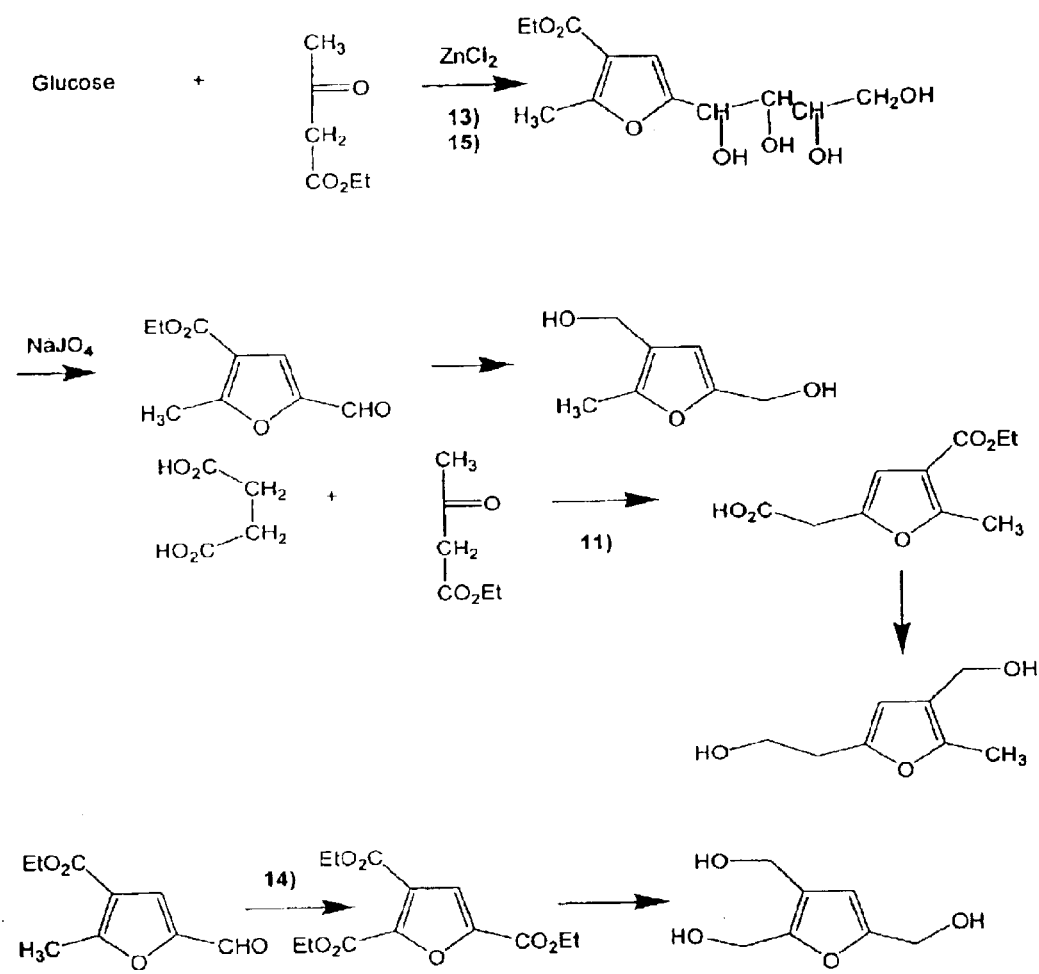

Literature Fig. 5(a) – 5(f):

1. M.C. Zaluski, M. Robba, M. Bonhomme Bull. Soc. Chim. France 1970, 1445-1450 (auch Aldehyd -> Nitril -> Aldehyd);
2. A. Toro, P. Deslongchamps Synthetic Communications 29 (13), 2317-2321 (1999);
3. R. G. Jones, J. Am. Chem. Soc. 77, 4069 (1955);.
4. M. Elliot, N.F. Janes, B.C. Pearson J. Chem. Soc. C 1971, 2552-2554;
5. T. Reichenstein, A. Grüssner, K. Schindler, E. Hardmeier Helv. Chim. Acta 16, 276-289 (1933)
6. R. A. Kretchmer, R.A. Latair J. Org. Chem. 43, 4596 (1978);
7. D.L. Dare, I.D. Entwistle, R.A.W. Johnstone J. Chem. Soc. Perkin I 1973, 1130-1134;
8. O. Moldenhauer J. Prakt. Chemie 330, 825 (1988)
9. C. Fayet, J. Gelas Carbohydr. Res. 155, 399-406 (1986);
10. O. Dann et al. Chem. Ber. 85, 457 (1952);
11. L.K. Dalton, Austr. J: Chem. 17, 1174-1181 (1964);
12. M. Valenta, P. Malon, M. Jandra, J. Srogl Collect. Czech Chem. Commun. 37, 493 (1972);
13. F. Garcia Gonzalez, Adv. Carbohydr. Chem 11, 97-144 (1956)
14. T. Szeki, E. Laszlo Chem. Ber. 73, 924-929 (1940);
15. J.K.N. Jones, J. Chem. Soc, 116-119 (1945)

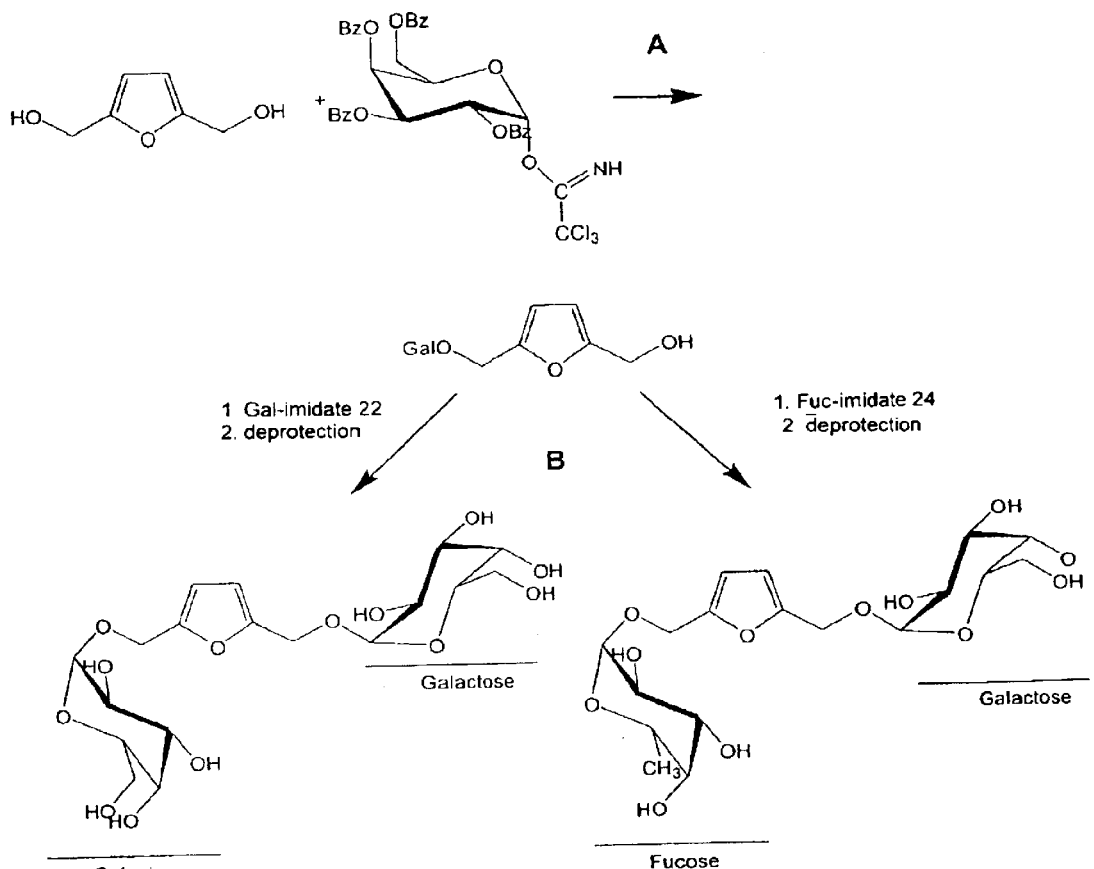
Fig. 6 Glycosidation of 2,5-bis-hydroxymethyl furan
Gal = Galactose; Fuc = Fucose

METHOD FOR PRODUCING WATER-SOLUBLE SACCHARIDE CONJUGATES AND SACCHARIDE MIMETICS BY DIELS-ALDER REACTION

The present invention relates to a method of preparing substance libraries on the basis of naturally occurring saccharides and saccharide mimetics.

As is known, the interactions between proteins and natural or synthetic oligosaccharides are highly specific. Substantially hydrogen bridge bonds, mutually present donors and acceptors as well as hydrophobic interactions are involved in these interactions. However, the binding constants thus achieved are less, by several orders, than those measured in the case of antigen-antibody interactions. In order to be able to optimize said interactions on the basis of saccharides and allow all kinds of interactions, a large number of substituted saccharides and saccharide mimetics have to be tested and synthesized. Here, the basic concept is the development of effective therapeutic agents on a saccharide basis. A major problem occurring in the synthesis of saccharide-containing compounds is, however, the complex multi-stage process implementation which in addition calls for a distinctive chemistry of protective groups. This will apply in particular if several saccharides shall be synthesized in and/or to a compound or if saccharide libraries shall be established. Therefore, there is the urgent need for a method with which even complex saccharide-containing compounds can be synthesized in a simple way. In particular, it is conceived to synthesize by this method saccharide clusters which are suited as therapeutic agents because they interact with receptors in and/or on cells or organs. Saccharide libraries and saccharide-containing compound libraries shall also be synthesized therewith. In addition, the method shall be suited to link saccharides with peptides, nucleic acids and/or lipids, a linkage of the polymers among themselves also being possible.

It is the object of the present invention to provide a method by which even complex saccharide compounds or libraries can be synthesized, as mentioned above.

This object is achieved by the subject matters defined in the claims.

The inventors developed a method of synthesizing saccharide compounds comprising the steps of:
(a) attaching at least one saccharide to a cyclic or acyclic diene,
(d) reacting the saccharide-containing diene obtained in step (a) or a commercially available saccharide-containing diene with a dienophile by Diels-Alder reaction.

The Diels-Alder reaction is a reaction in which a diene reacts with an olefin, a transitional state being passed through in which the 6Π electrons are involved. As compared to the conventional organic reactions this transitional state provides the Diels-Alder reactions with relatively low activation energies so that these reactions may already occur at room temperature or slightly elevated temperatures. Diels-Alder reactions may be accelerated by high pressure.

In the very past few years, a number of catalysts has become known which can catalyze effectively Diels-Alder reactions under mild conditions (K. Pindur et al., Chem. Rev. 1993, 93 pp. 741–761; Kündig et al., Angew. Chem. 1999, 111, pp. 1298–1301). Since Diels-Alder reactions are basically reversible, this reaction type is also suited for dynamic combinatorial chemistry. The formation of exo- and endo-isomers may be controlled via the temperature and also the catalyst. As to the yields the Diels-Alder reaction offers major advantages since it proceeds without further side-products and with almost quantitative yield. The Diels-Alder reaction is thus used by the inventors to synthesize complex saccharide compounds and libraries from saccharide-containing compounds and/or saccharide libraries. As a result, molecules which may contain three or even four different residues can be accessed when the two starting compounds (diene and dienophile) are skillfully substituted with functional groups or residues.

According to the invention the suitable cyclic diene component in step (a) is preferably furan, fulvene, furfural, cyclopentadiene, cyclohexadiene, pyrrole, 1,3-oxazole, 1,2-oxazole, pyrazole, thiophene and the acyclic compounds are preferably 1,3-dienes (e.g. trans-trans hexadiene-2,4-1,6-diol) which may be monosubstituted or polysubstituted with functional groups. The functional groups may be selected from e.g. alkyl chains ($C_2$–$C_{20}$, preferably methyl, ethyl, iso-propyl, tert-butyl, etc.), OH, SH, halogens, aryl, carboxyl, carbonyl, nitro, carboxyamido, keto, sulfoxide, sulfone, sulfonic acid, phosphoric acid or amino groups, which are bound directly or via alkyl residues. The diene component may also carry amino acid substituents, peptide substituents, lipid substituents or oligonucleotide and/or nucleic acid substituents. All kinds of pharmaceutical active substances, labelings, dyes or complexes (e.g. carborane, ferrocene) can be linked to the diene component.

Preferred diene components are: bishydroxyalkylfurans, such as 2,3-bishydroxymethyl furan, 3,4-bishydroxymethyl furan, 2,5-bishydroxymethyl furan, hydroxymethyl furfural, α-GMF (α-glycosylmethyl furfural; or aldehyde function reduced with $NaBH_4$, for example). Likewise the homologues thereof may also be used with an ethyl or propyl group in place of a methyl group. The diene components can be purchased from e.g. Aldrich company (furfural=Aldrich #27,886-6; hydroxymethyl furfural=Aldrich #4,080-7; 3-hydroxymethyl furan=Aldrich #19,639-8) or from S üdzucker A G (α-GMF). In general, 2,5-disubstituted furans in Diels-Alder reactions have less reactivity than 3,4-disubstituted ones. This graded reactivity can be utilized synthetically. Here, it is of advantage that the reactivity of hydroxymethyl groups differs in the individual furan positions so that sequential substitution becomes possible. Hence various saccharides can be introduced very simply into the furan (see FIG. 1). Cyclopentadiene and its substituted derivatives are also very well suited as dienes for the Diels-Alder reaction. Aldehyde derivatives of cyclopentadiene have long been known (Chem. Ber. 1964, 97, p. 2066) and can be converted step-wise into the hydroxymethyl compounds which according to the imidate method are reacted with saccharides and are then available as dienes. Carboxylic acid derivatives of cyclopentadiene are also known, such as esters, amides or nitriles (J. Chem. Soc. 1966, p. 1641). Here, cyclopentadiene-tetra-carboxylic acid carboxylic acid esters can also be prepared from the corresponding preliminary cyclopentane stages by dehydrogenation. These preliminary stages are, in turn, easily accessible from the Diels-Alder adducts from cyclopentadiene and maleic acid anhydride. Cyclization reactions of 1,3-diacarbonyl compounds also serve for preparing cyclopentadienes (J. Chem. Soc. 1952, p. 1127). Naturally occurring iridoid glucosides such as catapol and aucubin (Liebigs Ann. Chem. 1990, p. 715) may be considered preliminary stages for saccharide-substituted cyclopentadienes (THL 1997, 38, p. 6433). Besides, said glucosides may also be used as dienophiles for generating substance libraries to search for active substances.

In step (a) of the method according to the invention, a saccharide is linked with a diene by reacting the diene with an imidate component substituted with a saccharide. The reaction conditions for this reaction were described by R. R. Schmidt, in: Glycosciences, eds. H. J. Gabius, S. Gabius, pp. 31–53, for example. The saccharide can also be linked with the diene component by means of other reactions (e.g. by means of the known Koenigs-Knorr reaction). The term "saccharide" comprises saccharides of any kind, in particular monosaccharides, disaccharides, oligosaccharides or polysaccharides (e.g. monoantennal, diantennal, triantennal, multiantennal and dendritic saccharides) in all stereoisomeric and enantiomeric forms. They may be pentoses or hexoses which are available in the L-form or D-form. In particular glucose, very particularly α- and β-D-glucose, fructose, galactose, mannose, arabinose, xylose, fucose, rhamnose, digitoxose and derivatives thereof are preferred as monosaccharides. In particular saccharose, maltose, lactose or gentobiose, either 1,4-linked or 1,6-linked, and derivatives thereof are suited as disaccharides. Sugar alcohols, polyols, inositols and derivatives thereof, very particularly cis-insitol, epi-inositol, allo-inositol, myo-inositol, muco-inositol, chiro-inositol, neo-inositol, scyllo-inositol, pinpollitol, streptamine, quercitol, chinic acid, shikimic acid, conduritol A and/or B, validatol and quebrachitol, e.g. from galactinols of both vegetable sources, such as sugar beets (obtainable therefrom: hydroxymethyl furfural; F. W. Lichtenthaler, Mod. Synth. Meth. 1993, 6, pp. 273–376) and milk products or products obtained by enzymatic enantiomer separation are also considered saccharides herein. In addition, saccharides usable according to the invention are glycoconjugates. They may be conjugates of e.g. saccharides with peptides, lipids, acids (→ester), alkyl residues (→ether), heterocycles or other carbohydrates. An example of glycoconjugates is Z1–Z10, a mixture of 10 glycoconjugates. The Z1–Z10 compounds are naturally occurring glycopeptides, glycoproteins and lipopolysaccharides. Derivatives of said saccharides are e.g. saccharides protected with protective groups (e.g. benzoyl, silyl, dimethoxytrityl groups) and/or saccharides modified with functional groups such as amino, nitro, carboxy, carboxyamido, keto, sulfoxide, sulfone, sulfonic acid, phosphoric acid, phosphonic acid, mono/di/trialkylamide groups or halide groups. The above saccharides may occur in nature or be produced synthetically. The imidate preferably only has one saccharide but a number of 2, 3, 4, 5 and 6 saccharide components is also conceivable when the imidate is selected correspondingly. The saccharides may here be equal or differ from one another.

Preferred saccharide-substituted imidate components are tri-O-benzoyl fucoseimidate or tetra-O-benzoyl galactose-imidate. The saccharide-substituted imidate components are produced according to H. Paulsen et al., 1992, Liebigs Ann. Chem. 747–750, for example.

In order to obtain in step (a) a diene modified fully by saccharides, the predescribed reaction of the diene with the saccharide-substituted imidate may take place several times in succession (see Example 1) or the imidate is added in excess, singly or repeatedly saccharide-modified diene being separated from one another after the reaction to obtain uniform products in subsequent step (b). The compounds which can be produced in step (a) from the above preferred dienes and saccharide-substituted imidates are e.g. 3,4-bis-(fucosyl-oxymethyl)furan, 3,4-bis-(galactosyl oxymethyl) furan, 3-fucosyloxymethyl-4-galactosyloxymethyl furan, 2,5-bis-galactosyloxymethyl furan, 2,5-bis-fucosyloxymethyl furan, 2-fucosyloxymethyl-5-galactosyloxymethyl furan and alcohols, derived from furan-2,5-di-β-propionic acid or derived from furan-2,5-di-acetic acid. If the compounds contain protective groups (preferably: protective benzoyl groups) these may be cleaved e.g. using sodium methanolate solution according to standard methods.

In step (b), the suitable dienophiles are maleic acid (anhydride) derivatives, fumaric acid (anhydride) derivatives, maleinimide derivatives (preferably: N-substituted maleinimide), arcylic acid derivatives, acetylene derivatives, butyne dicarboxylic acid or its derivatives or enol ethers. In this connection, derivatives are those which following the substitution of said compounds carry alkyl chains ($C_2$–$C_{20}$), OH, SH, halogens, aryl, carboxy, carbonyl, nitro, carboxyamido, keto, sulfoxide, sulfone, sulfonic acid, phosphoric acid, amino, phosphonic acid or mono/di/trialkylamide groups. In addition, the dienophile component may be substituted with saccharides according to the above definition. The dienophile component may also carry amino acid substituents, peptide substituents, lipid substituents or oligonucleotide and/or nucleic acid substituents. All kinds of pharmaceutical active substance, labeling, dye or complex may be linked to the dienophile component. Preferred dienophiles are tris-(2-maleinimidoethyl)amine (TMEA), N-phenyl, N-ethyl, maleinimidolysine or conduritol.

One or both of the diene and dienophile components may contain aromatic or heterocyclic residues. These residues may be selected from: phenyl, thienyl, thiophenyl, furyl, furanyl, pyranyl, pyrrolyl, imidazolyl, pyrazolyl, pyridyl, pyrazinyl, pyrimidinyl, pyrazinyl, pyridazinyl, thiazolyl, oxazolyl, indolyl, furazannyl, pyrrolinyl, imidazolinyl, pyrazolinyl, thiazolinyl, triazolyl, tetrazolyl group as well as the positional isomers of the hetero atom or atoms which may comprise these groups, a residue consisting of carbocyclic annelated rings, e.g. the naphthyl group or the phenanthrenyl group, a residue consisting of annelated heterocyclic rings, e.g. benzofuranyl, benzothienyl, benzimidazolyl, benzothiazolyl, naphtho[2,3-b]thienyl, thianthrenyl, isobenzofuranyl, chromenyl, xanthenyl, phenoxathionyl, indolizinyl, isoindolyl, 3H-indolyl, indolyl, indazolyl, purinyl, quinolizinyl, isoquinolyl, quinolyl, phthalzinyl, naphthyridinyl, quinoxalinyl, quinazolinyl, quinolinyl, pteridinyl, carbazolyl, β-carbolinyl, cinnolinyl, acridinyl, phenazinyl, phenothiazinyl, phenoxazinyl, indolinyl, isoindolinyl, imidazopyridyl, imidazopyridimidinyl or also the annelated polycyclic systems consisting of heterocyclic monocycles, such as defined above, e.g. thionaphthenyl, furo[2,3-b]pyrrole or thieno[2,3-b]furan, and in particular the phenyl and furyl groups, such as 2-furyl, imidazolyl, such as 2-imidazolyl, pyridyl, such as 2-pyridyl, 3-pyridyl, 4-pyridyl, pyrimidinyl, such as pyridimid-2-yl, thiazolyl, such as thiazole-2-yl, thiazolinyl, such as thiazolin-2-yl, triazolyl, such as triazolyl-2,-yl, tetrazolyl, such as tetrazole-2-yl, benzimidazolyl, such as benzimidazole-2-yl, benzothiazolyl, benzothiazole-2-yl, purinyl, such as purine-7-yl, or quinolyl, such as 4-quinolyl.

The Diels-Alder reaction is a standard method of organic chemistry and the reaction conditions are well known to a person skilled in the art or can be looked up in relevant textbooks. Based on the present invention, the Diels-Alder reaction is carried out preferably in any solvents between 20° C. and 100° C. Preferred solvents are water or alcohols, such as methanol or ethanol. The formation of exo and endo compounds, as observed in this type of Diels-Alder reaction can be controlled by the experimental conditions and adds to the number of compounds obtained by a factor of two. This variation of the experimental conditions is within the skill of a person of ordinary skill in the art.

All Diels-Alder reactions are equilibrium reactions in which as a function of the temperature the components are also always present and thus can otherwise react with the other partners out of the equilibrium.

Thus, the above described system is also suited for the controlled release of the dienophile component, accompanied by the simultaneous attachment of the diene component to a polymer carrier or vice versa. If the dienophile carries e.g. a peptide or a therapeutic agent, a system will be available which can be utilized for the controlled and controllable release of medicaments from a solid phase. Extending the above described reactions, the method according to the invention will provide for a possibility of linking peptides with saccharides, peptides with nucleic acids, saccharides with nucleic acids and the respective component with itself if one component is linked with a diene and the other is linked with a dienophile. The resulting Diels-Alder adducts may be modified as such, e.g. by opening the anhydride ring or also by hydrogenation of the double bond or by addition reactions to this double bond.

The oxa-bicycloheptane ring system may be opened under acidic conditions to give a cyclohexane ring system. Here, a cleavage of the Diels-Alder adduct into the components is no longer possible and a new structural type, i.e. an inositol derivative, results, which certainly has different pharmacological properties since it no longer has the rigidity of the bicycle.

In order to establish greater clusters or libraries, steps a) and/or b) of the method according to the invention have to be carried out several times in succession.

Based on the present invention, step a) may, of course, be omitted when a saccharide-substituted diene is already used as a basis.

Some important aspects of the present invention shall be emphasized below, which shall not limit the broad method concept.

In the Diels-Alder reaction (scheme 1) a diene 1 is reacted with a dienophile 2.

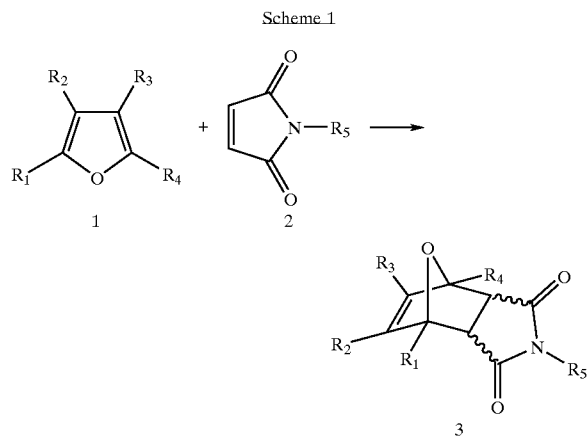

Scheme 1

Diene 1 (here: furan having the substituents $R_1$ to $R_4$) is in this case reacted directly with the dienophile 2 (here: maleinimide with the substituent $R_5$) in aqueous solution. This leads to a product mixture consisting of endo and exo Diels-Alder products 3. The composition of the product mixture can be controlled. It is also possible to separate endo and exo compounds from one another by means of chromatography. (Meanings of $R_1$ to $R_4$ and $R_5$: One or more substituents may be incorporated in all conceivable combinations. As to the definition of the residues: see above)

Thus, a description is given below which is initially about some possible preparations of dienes (of type 1, scheme 1) and their saccharide conjugates, then about the dienophiles (of type 2) and finally about the Diels-Alder reaction.

Preparation of the Dienes (Preferably Furan Derivatives):

Saccharide-modified furan derivatives are produced in accordance with the concept of the invention. Suitable compounds are thus furan derivatives containing a hydroxy group (removed from the ring directly or by a spacer) which permits the covalent, glycosidic linkage with a saccharide molecule (e.g. $R_1=CH_2$—OH). The possible syntheses for this purpose are numerous and usually known from the literature.

The following reaction schemes (FIGS. 5(a)–(f)) are given as examples to show the ease of accessibility of the required furan derivatives and the efficiency of the synthetic pathways.

Along with the presented synthetic pathways there are even other variants already known from the literature. The dienes described here are listed by way of example. Besides, there are also other dienes which following conjugation with saccharides were used by inventors in Diels-Alder reactions. They are shown below in a table.

Synthesis of the Saccharide-containing Dienes

The furan derivatives are linked covalently with saccharides preferably according to the imidate method (scheme 3, see FIG. 6). In the first step of the reaction (A), simple galactosidation is achieved by reacting in each case 1 equivalent of furan derivative with 1 equivalent of galactoseimidate. The mono-galactosidated compound is purified by means of chromatography. In a second step of the reaction (B), 1 equivalent of another glycosylimidate is added. A double reaction with Gal-imidate serves for obtaining a compound with two galactose units after separating the protective groups. However, if fucose imidate is used in step B, a mixed glycosidated furan derivative is obtained after cleaving the protective groups. The entire reaction may also take place by Koenigs-Knorr reaction or other methods known in the literature.

Combinatorial Analysis with Furan Saccharides

Reaction of 2,3,4-trishydroxyfuran (or other "polyhydroxylated" furan derivatives) using three times the molar amount of the mixture of 10 different imidates in equal proportions. Cleavage of the protective groups and Diels-Alder reaction with a labeled maleinimide in excess. Isolation of the labeled library and test on fixed cells. The structures having optimum effects can be detected by variation of the saccharide imidates, addition and omission and their concentrations.

If a furan substituted twice with sugar residues is used as a diene and an N-substituted maleinimide carrying a saccharide over a spacer of any length is used as a dienophile, trisaccharides will form in the Diels-Alder reaction. Following this scheme a library having almost 1000 different trisaccharides can be generated when e.g. ten different saccharide imitates are used. Since the protective groups of both the diene and the dienophile can be cleaved beforehand, the Diels-Alder reaction may be carried out in water, which has a favorable effect on the reaction rate and yield (see FIG. 2).

By means of the method according to the invention, substances/libraries can be prepared which are suited to inhibit the interaction of lectins with proteins. Such substances can be used in oncotherapy to avoid metastases or as antiphlogistics. The use of spacers—which can be inserted in both the diene and the dienophile—or of rare saccharides or saccharides provided with unusual functional groups, increases the diversity of the libraries. The multiantennal characteristic which may be of significance for the interaction of saccharides with lectins, can also be produced by means of the method according to the invention.

Figure 3:
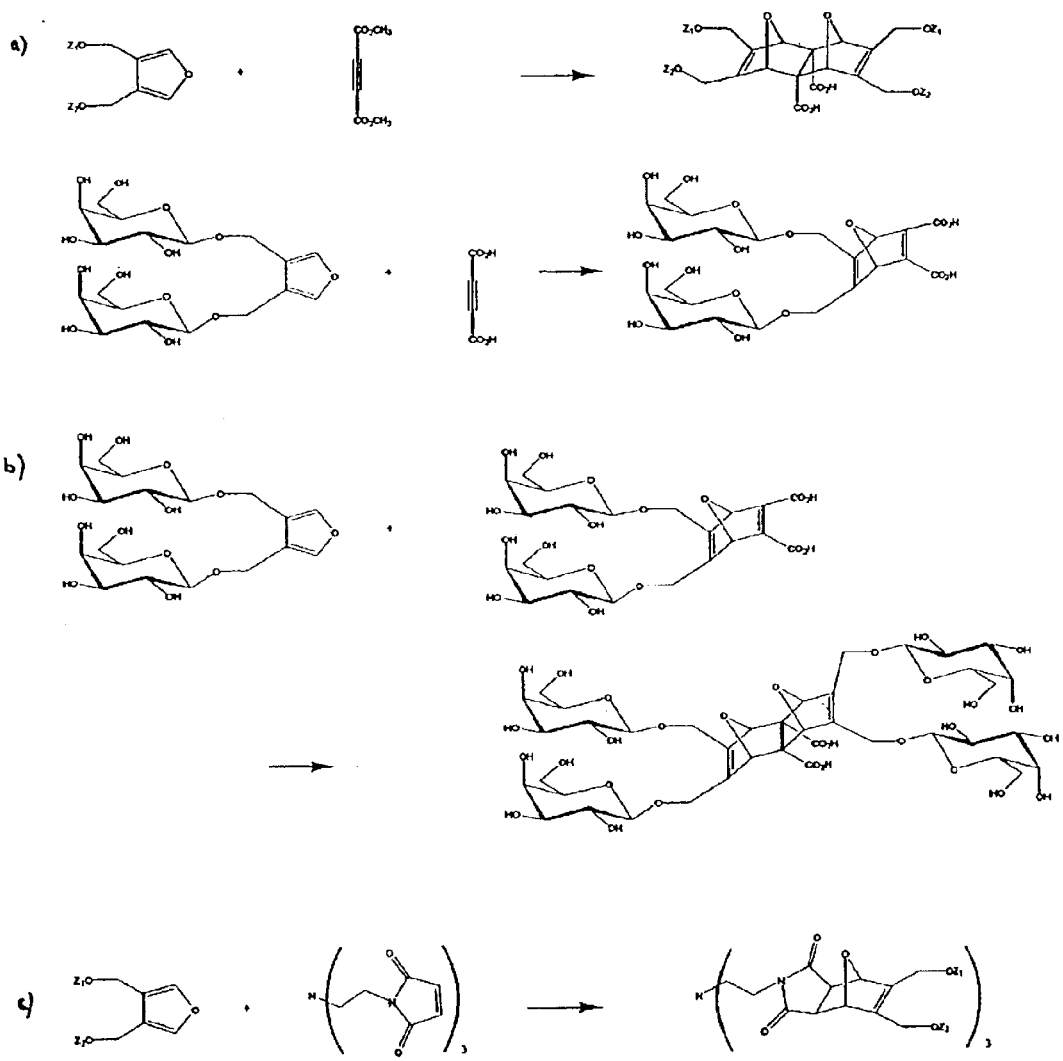

Due to the double or triple Diels-Alder reaction with a corresponding dienophile such molecules are easily accessible (see FIG. 3).

Compounds/libraries can be generated by the method according to the invention, which in addition to the saccharides also contain other pharmacophore groups to render general access to new central structures for therapeutic agents. Such groups may be heterocycles, aromatics or also peptide structures which are contained in either the diene or the dienophile. The diversity of the libraries is considerably increased by these many and diverse possible combinations. In this connection, the often low conformative movability of the resulting Diels-Alder products may be favorable since such structures can better attach to receptors. As a result of the presence of the saccharide residues in the products, the latter are correspondingly water-soluble.

Figure 2:
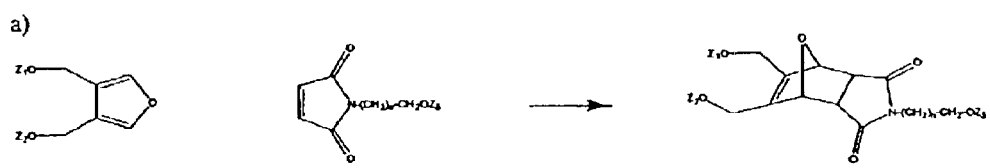
Figure 2:
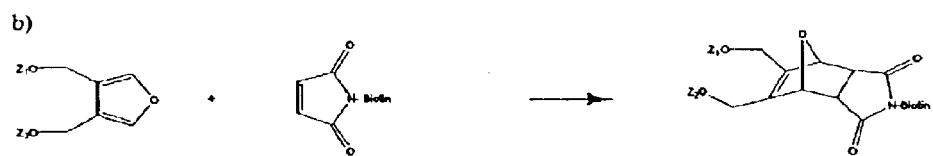

The Diels-Alder reaction of dienes with dienophiles (e.g. substituted maleinimides) can also be used to link proteins with saccharides and saccharides with nucleic acids. Here, it is useful to have a lysine residue which enables the attachment of the maleinimide residue through the free amino group. However, it is also conceivable that a lysine residue is attached to the amino-terminal end. The influence of different (oligo)saccharides on the effectiveness of the proteins or their pharmacokinetics can be studied with these neo-glycoproteins accessible in this way. Labeling of saccharides with biotin can also be carried out without any problems in the same way, which was important for a possible diagnosis on the basis of lectin-saccharide interactions (FIG. 2).

The Diels-Alder reaction of dienes (e.g. substituted furans) with dienophiles (e.g. substituted maleinimides) also results in the doping of surfaces with saccharides, lipids, peptides or (oligo)nucleotides. Here, both the dienophile and the diene may be immobilized on the surface. Application for chip technology is thus conceivable. The increase in the charging density on the surface is also possible by using structures as in FIG. 2.

Since the Diels-Alder reaction with these components can very well be carried out in water and usually does not require catalysis, all of the components can be reacted with one another without protective groups. The final cleavage of protective groups, a process which often creates major difficulties, is thus omitted.

Since all of the Diels-Alder reactions are reversible and the equilibriums already adjust at room temperature, the reversal of the adduct formation can also be used for the controlled release of the components of the Diels-Alder reaction charged with active substances for this purpose.

As already explained in the introductory part, the natural binding constants between proteins and (oligo)saccharides are not very high. Based on evolution there was obviously no need for a further optimization of these binding constants. For fundamental considerations it should be possible to prepare effective agonists and antagonists of receptors in analogy to peptides by allowing all kinds of interactions, including ionic interactions, on the basis of saccharides and saccharide mimetics. The use of substituted saccharides, all kinds of functional groups being usable, also those formerly not occurring in saccharides, is certainly a precondition for this optimization.

By means of combinatorial chemistry it is possible to identify very effective agonists and antagonists on the basis of peptides, lipids or nucleic acids. In order to develop therefrom therapeutic agents, above all for oral application, substances are required which are orally available. The necessary precondition for this is the sufficient water solubility. A possible approach for improving the water solubility and thus the oral availability is the covalent linkage of active substances with saccharides, forming conjugates. Using the approach according to the invention it is possible to consider the problem of adequate water solubility by using suitable building blocks from the very beginning by means of a combinatorial approach. This also offers the advantage that these building blocks on the basis of saccharides and their derivatives become part of the active substance and can thus contribute to strengthening the attachment of the active substance to its target. The inventors also took into account to transmit the method to the solid phase, the attachment to the solid phase usefully taking place through the saccharide portion.

The invention is further described by means of the below figures.

FIG. 1: introduction of 2 saccharide residues into a furan system

FIG. 2: reaction of a disubstituted furan with an N-substituted maleinimide

FIG. 3: Multiple Diels-Alder reaction

Figure 4:
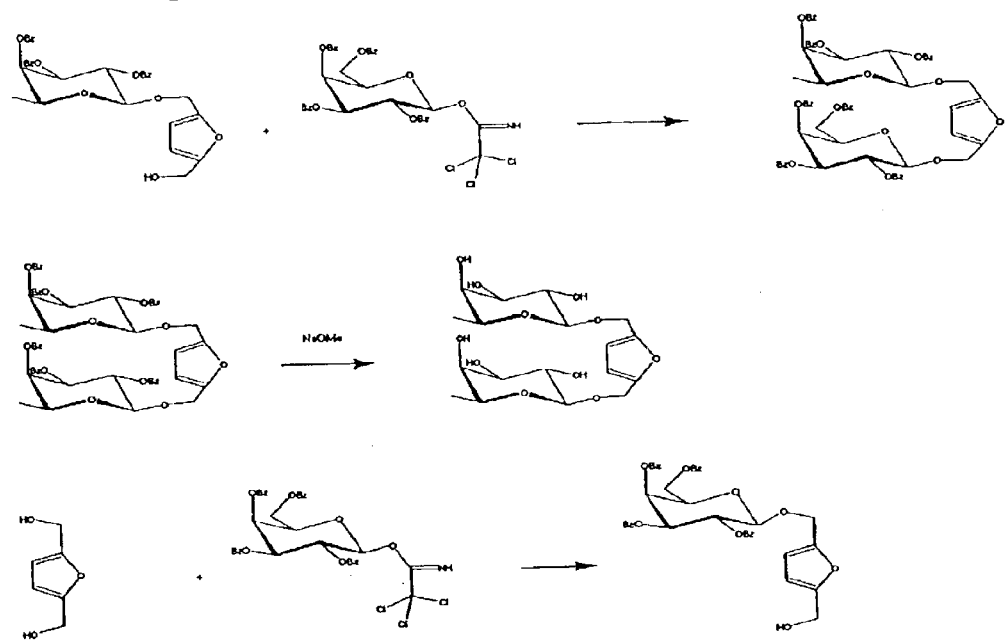

FIG. 4: illustrative building blocks for the Diels-Alder reaction

FIG. 5(a)–(f): Preparation of furan derivatives which can be conjugated with saccharides FIG. 6: glycosidation of 2,5-bis-hydroxymethylfuran The invention is further clarified by means of the below examples.

EXAMPLE 1

Synthesis of Glycosidated Hydroxymethyl Furans

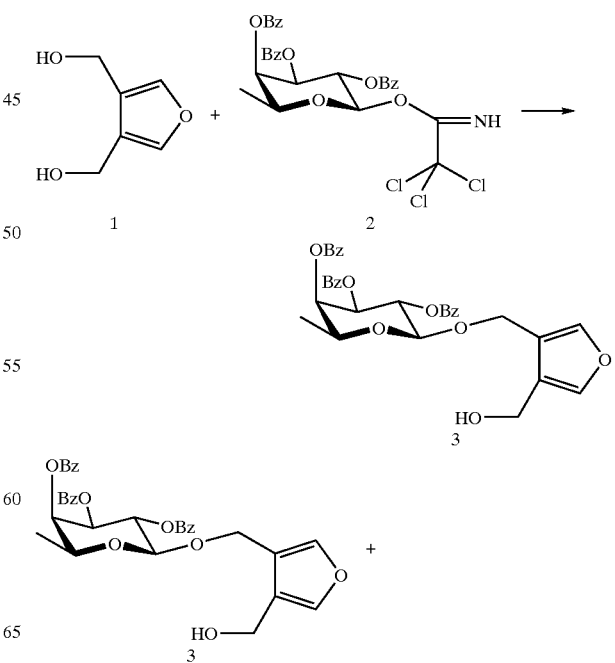

-continued

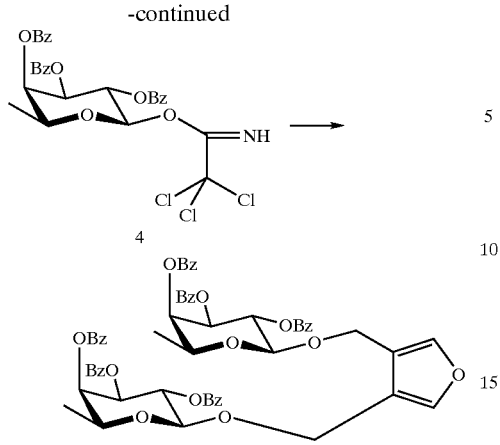

EXAMPLE 2
Glycosidation of Maleinimide and/or Derivatives

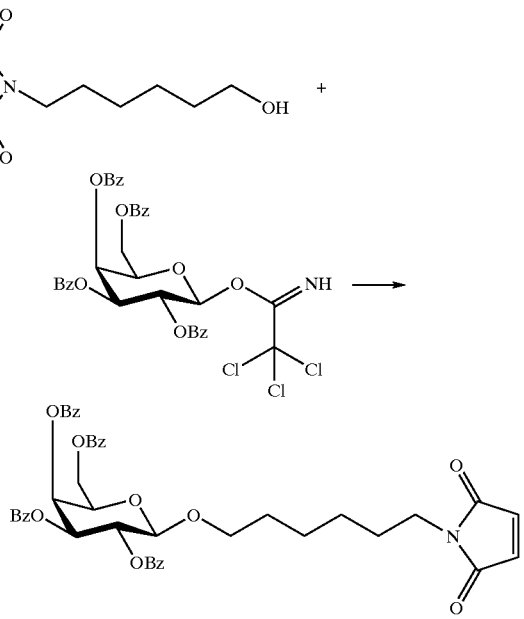

20 mmol 3,4-bis-hydroxymethylfuran 1 and 21 mmol tri-O-benzoyl-fucose-imidate 2 are dissolved in 300 ml dichloromethane. The solution is cooled to −40° C. and admixed with several drops of triflat. The reaction solution is then stirred in an ice bath for 1 hour, the organic phase is shaken out with dilute bicarbonate solution and then with water, dried on sodium sulfate and concentrated in vacuo. Following column chromatography on silica gel with petroleum ether/acetic ester (2/1) the reaction product 3 is obtained in a yield of about 60%.

6 mmol mono-fucosylated furan 3 are reacted with 6.3 mmol imidate 4 as described above. The purification is effected by means of column chromatography on silica gel with petroleum ether/acetic ester (2/1). The product 5 is obtained in a yield of about 55%.

For the deprotection (cleavage of the benzoyl groups) the product 5 was reacted with sodium methanolate solution.

Yields: about 60%.

In order to produce the corresponding 2,5-products, 2,5-bis-hydroxymethylfuran in place of 3,4-bis-hydroxymethylfuran is reacted in the first step and the analogous steps are taken as outlined above.

5 mmol of suitably derivatized maleinimide 1 (maleinimide+spacer+OH) are dissolved with 4.9 mmol galactosylimidate 2 in 100 ml dichloromethane and admixed with 10 drops of triflat at −40° C. Stirring is carried out at 0° C. When the reaction is finished, the reaction solution is shaken out with dilute bicarbonate solution and water. The solvent is dried on sodium sulfate and concentrated in vacuo. The residue is chromatographed on silica gel with petroleum ether/acetic ester (2/1). Yield of product 3: 54%.

For cleaving the benzoyl groups, sodium methanolate or a mixture of methanol/water/triethylamine is used for the reaction.

EXAMPLE 3
Diels-Alder Reaction a) Biotinylation

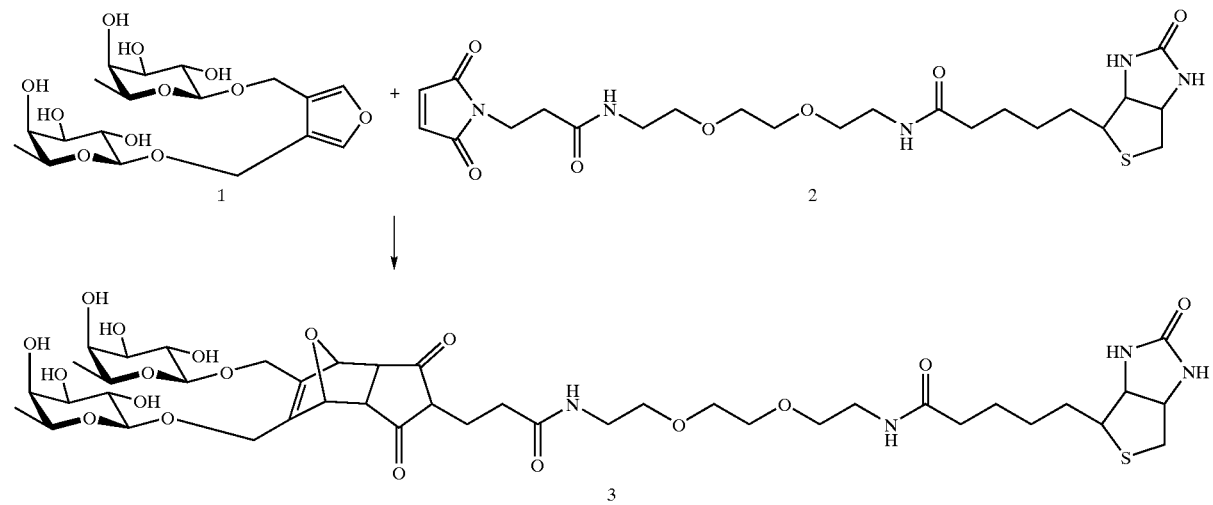

-continued

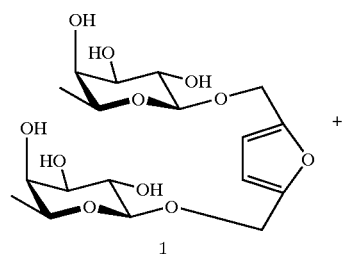

1

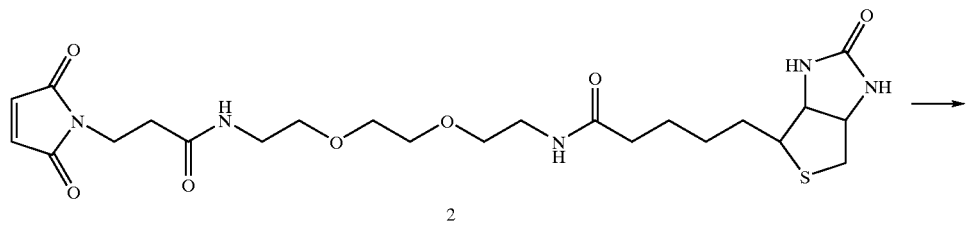

2

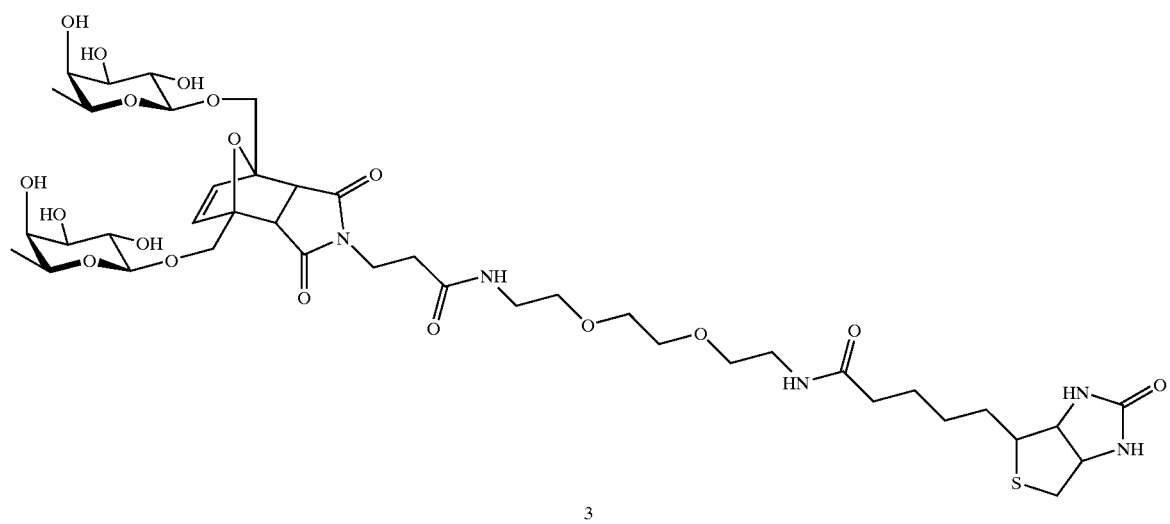

3

50 μmol glycosidated furan 1 (see Example 1) and 50 μmol biotin derivative 2 (Pierce company, catalog number 2 1900 ZZ) are dissolved in 1 ml water. The solution is stirred at room temperature. The reaction proceeds while controlled using HPLC. When the reaction is concluded, the reaction solution is freeze-dried. The product 3 (endo/exo mixture) is isolated by means of preparative HPLC. Yield 50–60%.

b) The following reactions were also carried out under the same conditions, each diene component being prepared according to Example 1 and the dienophile component being prepared according to K. Wakisaka et al., J. Med. Chem. 1997, 40, pp. 2643–2652.

Introduction of a Lysine Residue:

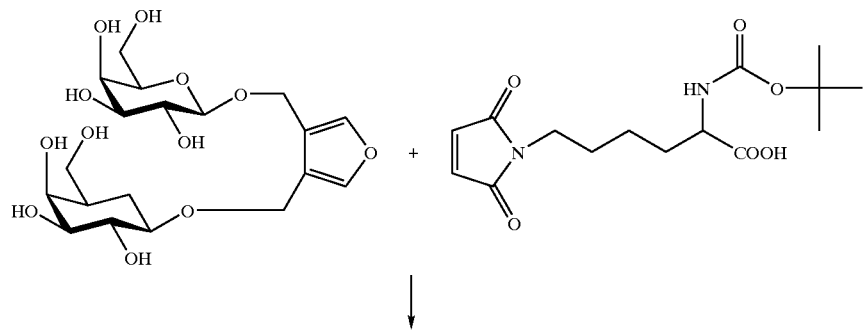

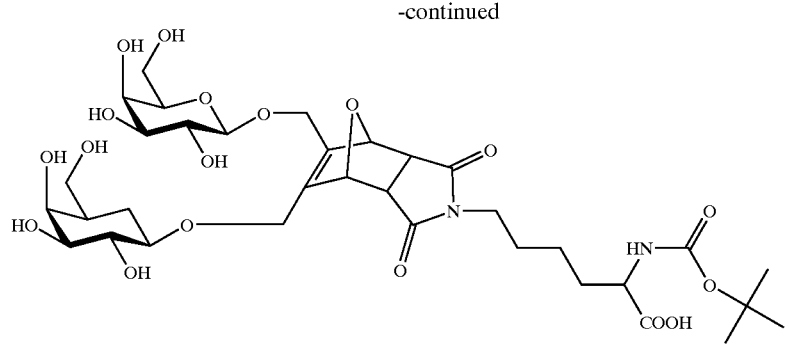
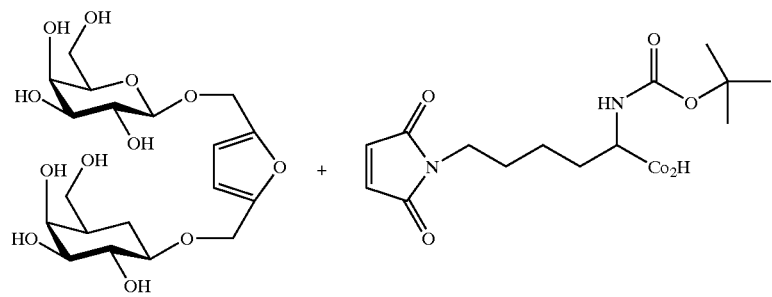
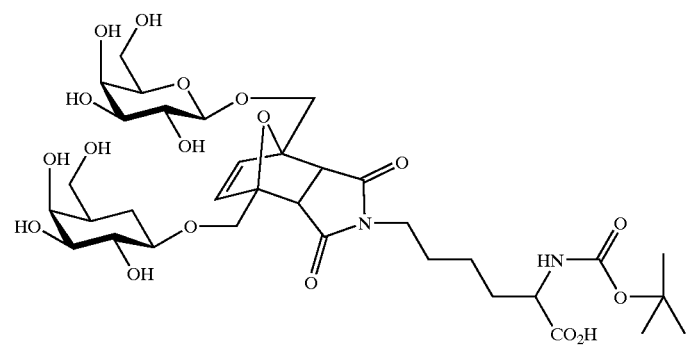
c) Reaction of 2,5- and 3,4-glycosyl-hydroxymethylated furans
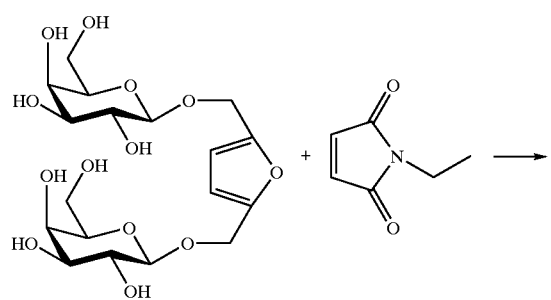
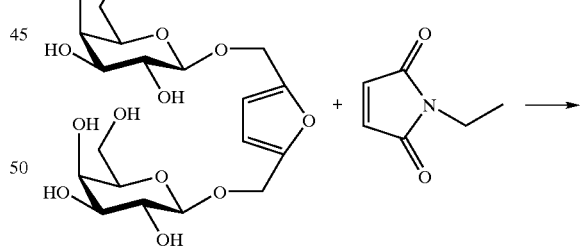
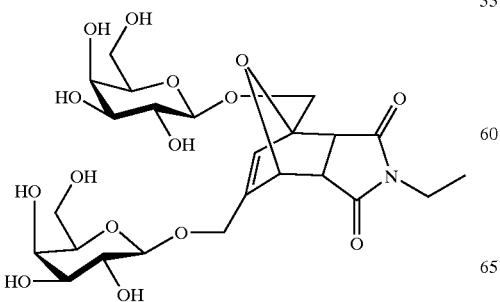
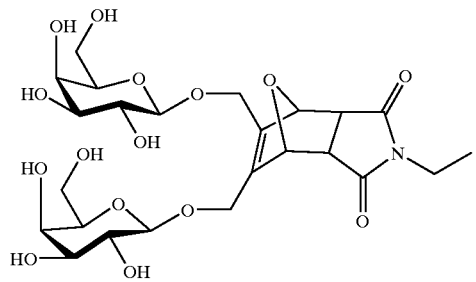

EXAMPLE 4
Preparation of Glycoclusters by Means of Diels-Alder Reaction
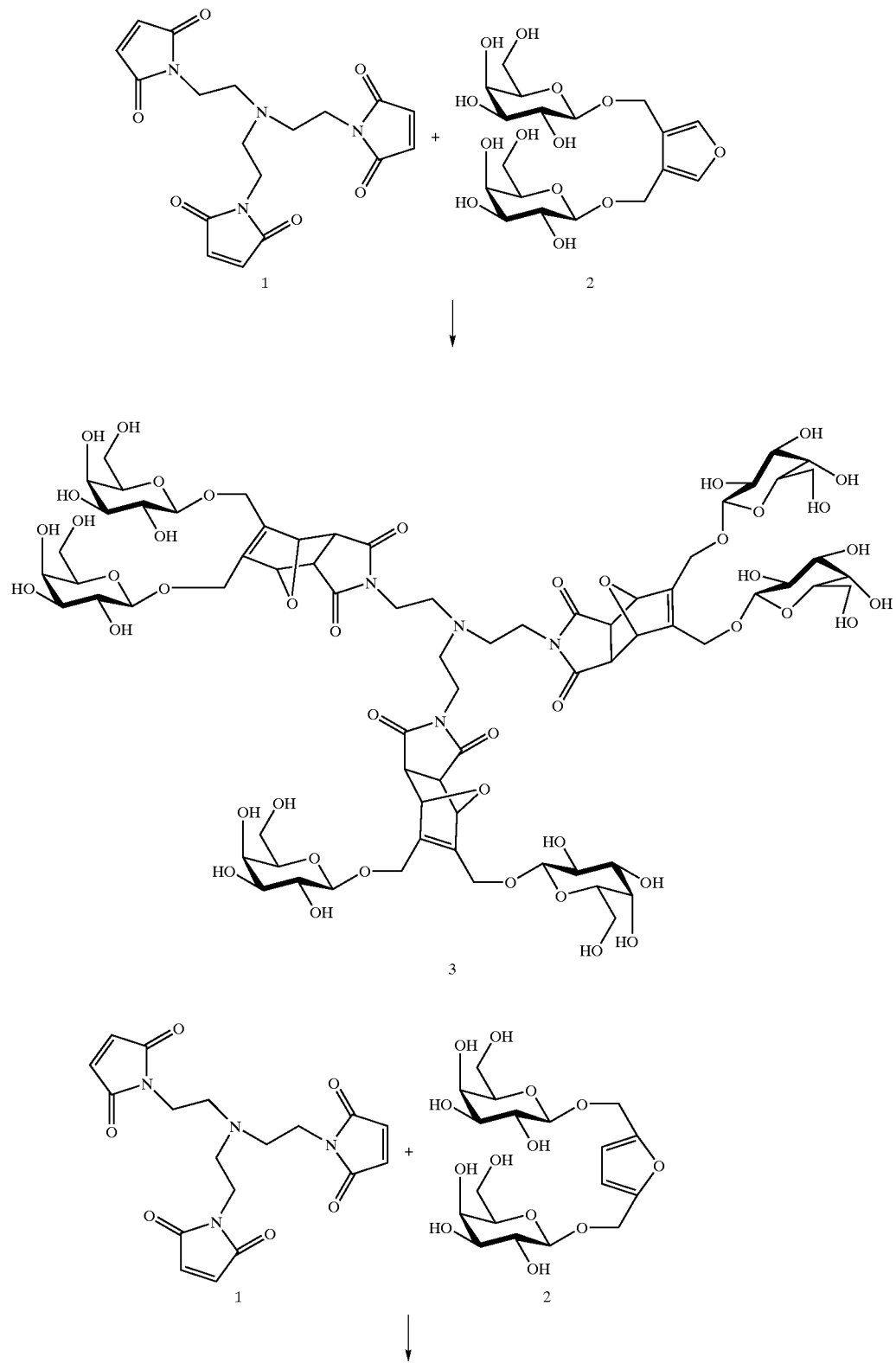

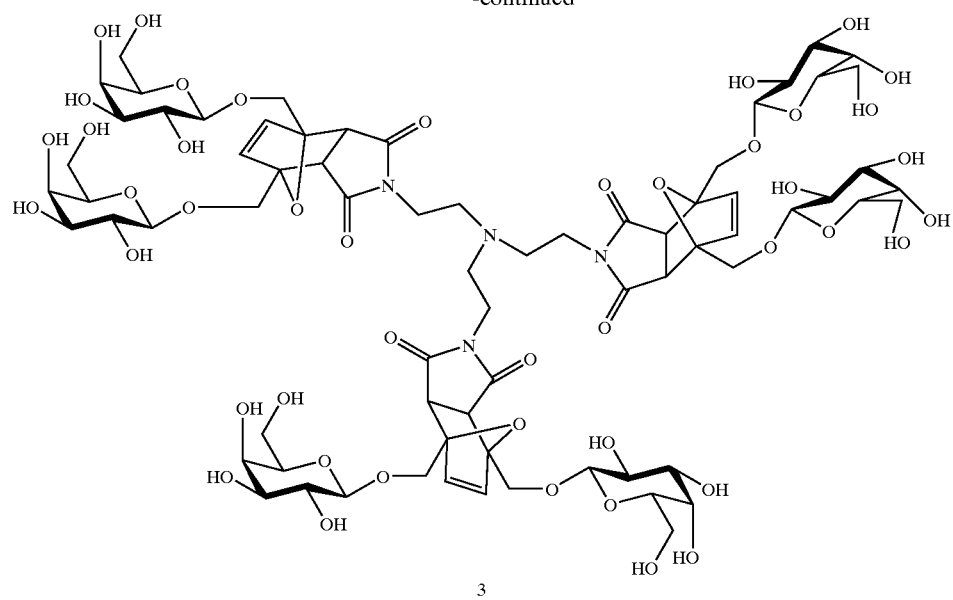

3

A solution of 50 μmol tris(-2-maleinimidoethyl)amine 1 (TMEA) and 190 μmol bis-galactosyl furan 2 in 1 ml water is stirred at room temperature for 50 hours. The product mixture 3 (combination or endo and exo products) is obtained by means of HPLC in yield of about 30%.

EXAMPLE 5

Crossed Diels-Alder Reaction

This relates to the simultaneous reaction of 2,5- and 3,4-furans with a dienophile (→combinatorial analysis)

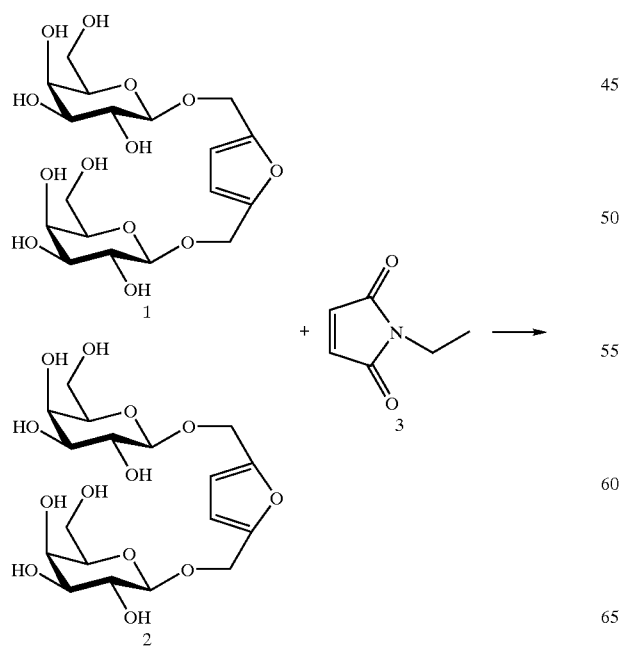

-continued

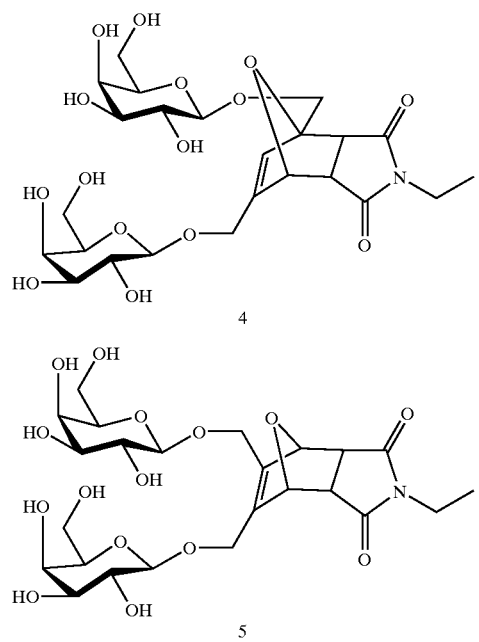

50 μmol of a mixture of the glycosidated 3,4- and 2,5-furans 1, 2 (see Example 1) and 50 μmol N-ethyl maleinimide 3 are dissolved in 1 ml water. The solution is stirred at room temperature. The reaction proceeds while controlled using HPLC. When the reaction is concluded, the reaction solution is freeze-dried. Products 4 and 5 are isolated by means of preparative HPLC. Yield 50–60%.

EXAMPLE 6

Diels-Alder Reaction on the Solid Phase

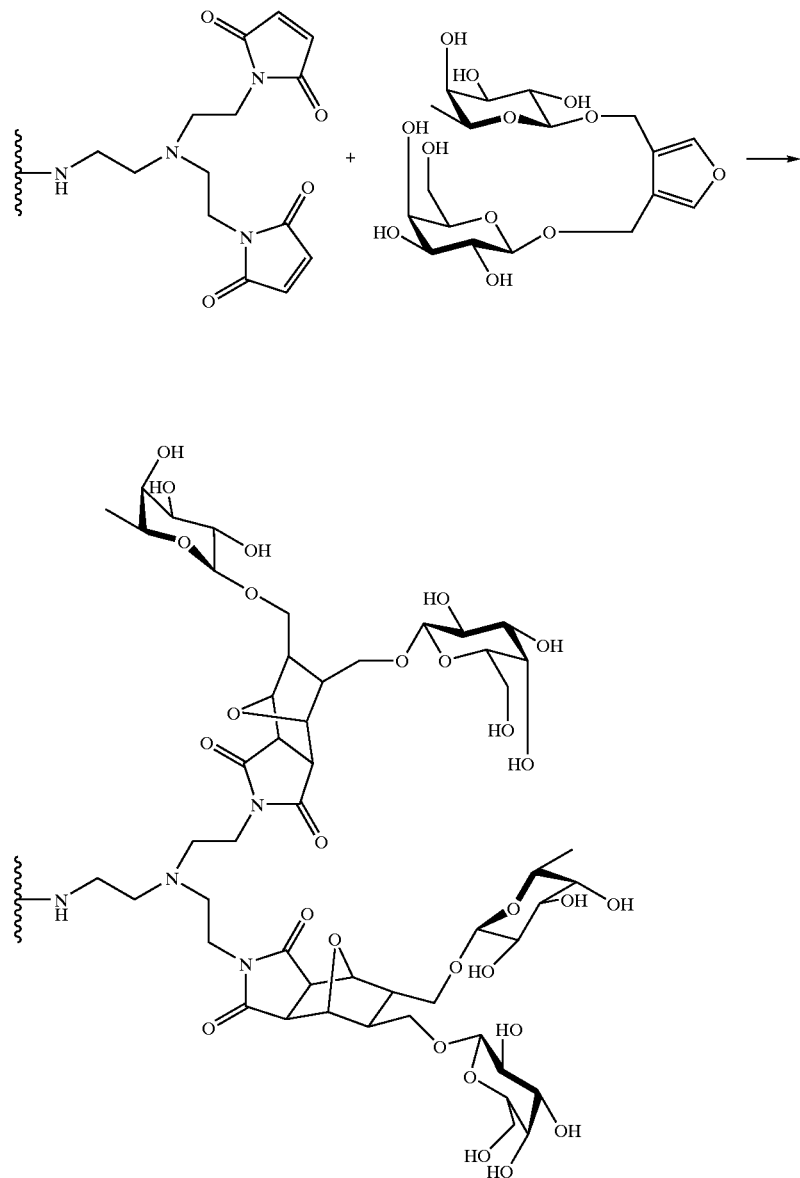

1.0 g tris-(2-aminoethyl)amine polymer (Aldrich #47, 210-7) are allowed to swell in 20 ml water for 1 hour. Thereafter, slurrying in 20 ml saturated $NaHCO_3$ solution takes place and the slurry is mixed with 1080 mg methoxycarbonyl maleimide at 0° C. and then stirred at room temperature for 16 hours. A pH of 3–4 is adjusted using $H_2SO_4$, extraction is carried out using acetic ester and dichloromethane. The aqueous phase is dried. 108 mg glycosylated furan derivative (see Example 1) is added to 100 mg of the product in 3 ml water. Stirring is carried out at room temperature. After 16 hours, the water is removed and the product is purified by means of HPLC.

EXAMPLE 7

Preparation of Trisaccharides

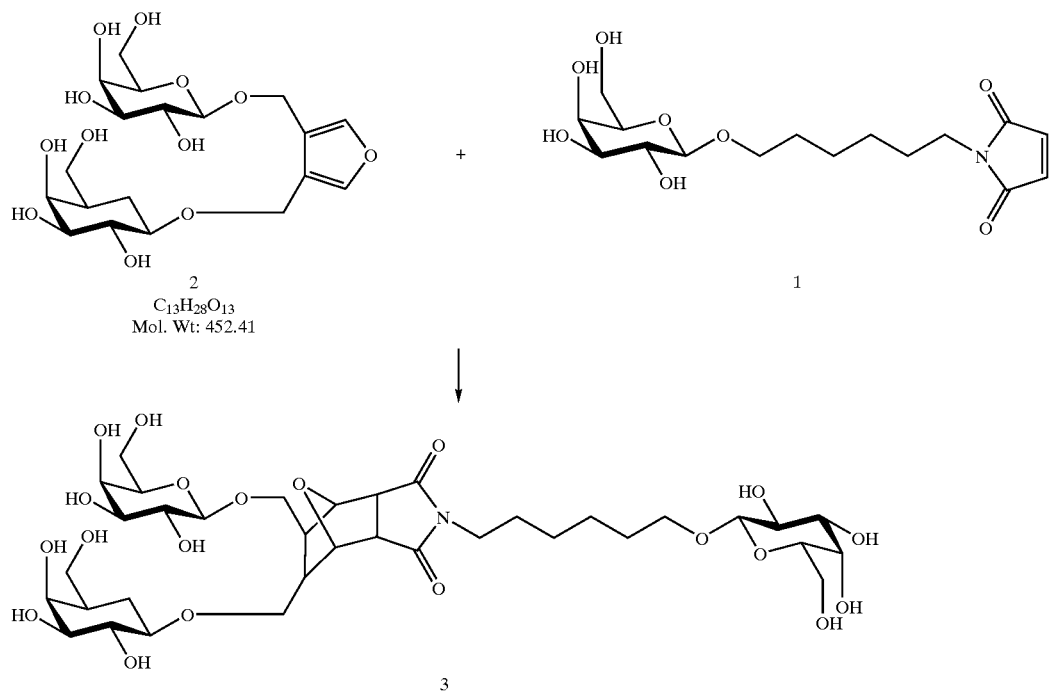

5 mmol of suitably derivatized maleinimide 1 (maleinimide+spacer+saccharide) are dissolved with 4.9 mmol diglycosylated furan 2 in 100 ml dichloromethane and admixed with 10 drops triflat at −40° C. Stirring is carried out at 0° C. When the reaction is completed, the reaction solution is shaken out with dilute bicarbonate solution and water. The solvent is dried on sodium sulfate and concentrated in vacuo. The residue is chromatographed on silica gel with petroleum ether/acetic ester (2/1). Yield of product 3: 54%.

EXAMPLE 8

Glycosidation of Furan Derivatives with Hydroxy Functions (a) Method A: Monoglycosidation

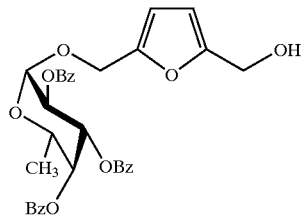

2,5-Bishydroxymethyl furan (2 mmol, 265 mg) and 2,3,4-tri-O-benzoylfucseimidate (2 mmol, 1.28 g) are admixed with 5 drops triflat in 50 ml dichloromethane at −40° C. and then stirred at 0° C. for 1 hour. The reaction solution is stopped by adding dilute aqueous bicarbonate solution. The organic phase is washed with 20 ml water and after drying on sodium sulfate concentrated in vacuo. The residue is chromatographed on silica gel (petroleum ether/acetic ester: 2/1).

Yield 700 mg (60%); ESI-MS: [M+H$^+$]: 58611

This compound can then be reacted in a second reaction once again with an equivalent of any saccharide imidate.

(b) Method B: Multiple Glycosidation

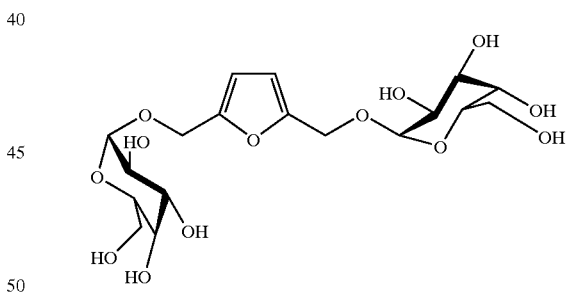

2,5-Bishydroxymethyl furan (2 mmol, 265 mg) and 2,3,4,6-tetra-O-benzoylgalactoseimidate (4 mmol, 1.48 g) are admixed with 5 drops triflat in 50 ml dichloromethane at −40° C. and then stirred at 0° C. for 2 hours. The reaction solution is stopped by adding dilute aqueous bicarbonate solution. The organic phase is washed with 20 ml water and after drying on sodium sulfate concentrated in vacuo. The residue is chromatographed on silica gel (petroleum ether/acetic ester: 2/1).

Yield: 1.4 g (55%); ESI-MS: [M+H$^+$]: 1284.3

For cleaving the protective groups the compounds are reacted in methanolic solution with sodium methanolate. The saponification is effected quantitatively.

If the furan derivative contains several hydroxyl functions which can be glycosidated, the reaction will be carried out for step-wise glycosidation according to method A.

However, if only one carbohydrate species shall be conjugated to all of the available hydroxyl functions, method B will be used.

In this way, the following furan derivatives were prepared:

3-Hydroxymethylfuranglycoside

R₁O—[furan]

| R₁ |
|---|
| Glucose |

2,3-Bishydroxymethylfuranglycoside

R₂O—[furan]—CH₂OR₁ (structure with R₂O at 3-position, R₁OCH₂ at 2-position)

| R₁ | R₂ |
|---|---|
| Fucose | OH |
| Galactose | OH |
| Fucose | Fucose |
| Galactose | Galactose |

2,4-Bishydroxymethylfuranglycoside

R₁OCH₂—[furan]—CH₂OR₂

| R₁ | R₂ |
|---|---|
| OH | Fucose |
| Fucose | Fucose |
| Galactose | Galactose |

3,4-Bishydroxymethylfuranglycoside

R₁O—[furan]—OR₂

| R₁ | R₂ |
|---|---|
| Fucose | OH |
| Galactose | OH |
| Fucose | Fucose |
| Galactose | Galactose |
| Galactose | Fucose |
| Lactose | Lactose |
| Glucose | Glucose |
| sialic acid | OH |
| sialic acid | Fucose |
| sialic acid | sialic acid |

3-Hydroxymethylfuranglycoside

R₁O—[furan]

2,5-Bishydroxymethylfuranglycoside

R₁O—[furan]—OR₂

| R₁ | R₂ |
|---|---|
| Fucose | OH |
| Galactose | OH |
| Glucose | OH |
| Fucose | Fucose |
| Galactose | Galactose |
| Galactose | Fucose |
| Lactose | Lactose |
| Glucose | Glucose |
| sialic acid | OH |
| sialic acid | Fucose |
| sialic acid | sialic acid |

2,3,4-Trishydroxymethylfuranglycoside

R₂O—[furan]—OR₃, R₁O—

| R₁ | R₂ | R₃ |
|---|---|---|
| Galactose | Galactose | Galactose |
| Fucose | Fucose | Fucose |

2,3,5-Trishydroxymethylfuranglycoside

FucO—[furan]—OFuc, FucO—

| R₁ | R₂ | R₃ |
|---|---|---|
| Fucose | Fucose | Fucose |

Others:

FucO—[furan]—OFuc with CH₃

EXAMPLE 9

Preparation of Dienophiles

Numerous maleinimide-type dienophiles have been synthesized. However, some are also commercially available.

General Maleinimide Syntheses:

Synthesis of N-(methoxycarbonyl)maleinimide: O. Keller, J. Rudinger, Hel. Chim. Acta 1975, 58, 531541.

J. T. Elliott, G. D. Prestwich, Bioconjugate Chemistry 2000, 11, 832–841.

S. Kalgutkar, B. C. Crews, L. J. Marnett, J. Med. Chem. 1996, 39, 1692–1703.

M. Dörr, R. Zentel, R. Dietrich, K. Meerholz, C. Bräuchle, J. Wichern, S. Zippel, P. Boldt, Macromolecules 1998, 31, 1454–1465.

N-dodecyl Maleinimide

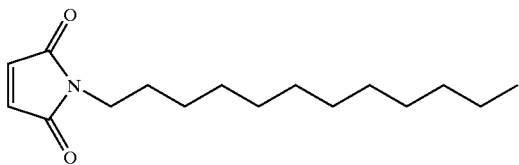

300 mg (1.62 mmol) dodecylamine are dissolved in 10 ml CHCl3 and cooled to 0° C. The solution is mixed with N-methoxycarbonylmaleinimide (NMM, 507 mg, 3.24 mmol) and tetrabutylammonium hydrogensulfate (503 mg, 1.48 mmol). Triethylamine (0.3 ml, 2.16 mmol) is slowly added and stirring is carried out at 0° C. for another 10 minutes. The ice bath is removed and 20 ml saturated NaHCO3 solution is added. Following 3 hours at room temperature, the reaction mixture is extracted using acetic acid ethyl ester (3×50 ml). The combined organic extracts are washed once with saturated NaCl solution. The organic phase is dried with magnesium sulfate and the solvent is removed in vacuo. N-dodecylamine is then purified by chromatography on silica gel (petroleum ether/EtOAc 10:1) and obtained as a colorless solid.

Yield: 365 mg (85%)

1H NMR (250 MHz, CDCl3): δ=0.88 (t, J=6.6 Hz, 3H), 1.25 (br. s., 16H), 1.54–1.60 (m, 4H), 3.50 (t, J=7.3 Hz, 2H), 6.67 (s, 2H).

N-stearyl Maleinimide

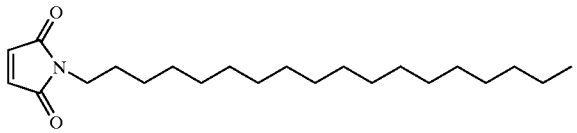

500 mg (1.85 mmol) stearylamine are dissolved in 10 ml CHCl3 and cooled to 0° C. N-methoxycarbonylmaleinimide (NMM, 580 mg, 3.71 mmol) and tetrabutylammonium hydrogensulfate (574 mg, 1.69 mmol) are added. Triethylamine (0.34 ml, 2.46 mmol) is slowly added and stirring is carried out at 0° C. for another 10 minutes. The ice bath is removed and 20 ml saturated NaHCO3 solution is added. After 3 h at room temperature, the reaction mixture is extracted using acetic acid ethyl ester (3×50 ml). The combined organic extracts are washed once with saturated NaCl solution. The organic phase is dried with magnesium sulfate and the solvent is removed in vacuo. N-stearylamine is then purified by chromatography on silica gel (petroleum ether/EtOAc 10:1) as a colorless solid.

Yield: 515 g (80%)

1H NMR (250 MHz, CDCl3): δ=0.88 (t, J=6.6 Hz, 3H), 1.25 (br. s., 28H), 1.50–1.60 (m, 4H), 3.50 (t, J=7.3 Hz, 2H), 6.67 (s, 2H).

ESI-MS: [M+H+] 350.0

N-cholesteryl Maleinimide

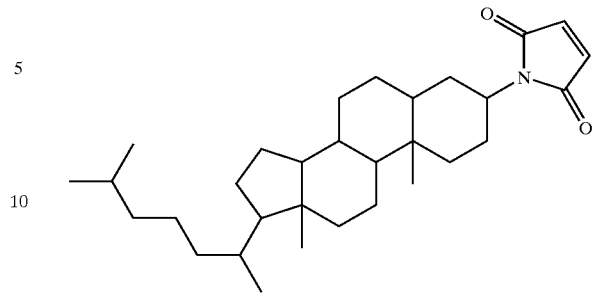

Cholesterylamine (1.0 g, 2.58 mmol) is dissolved in CHCl3 (50 ml) and mixed with maleic acid anhydride (253 mg, 2.58 mmol). Stirring is carried out overnight and the solvent is then removed in vacuo. The residue is taken up in acetic acid anhydride (30 ml) and mixed with sodium acetate (300 mg). The reaction mixture is stirred at 100° C. for 4 h and then poured onto 100 ml ice water. Extraction is carried out with acetic acid ethyl ester (3×100 ml) and the organic phase is washed with saturated NaCl solution (1×100 ml). The organic phase is dried using magnesium sulfate and the solvent is removed in vacuo. The residue is purified by chromatography on silica gel (petroleum ether/EtOAc 7:1). N-cholesteryl maleinimide is obtained as a colorless oil.

ESI-MS: [M+H+] 468.3

Synthesis of cholesterylamine: R. Krieg, R. Wyrwa, U. Möllemann, H. Görls, B. Schönecker, Steroids, 1998, 63, 531–541; M. Hasan, N. Rashid, K. M. Khan, G. Snatzke, H. Duddeck, W. Voelter, Liebigs Ann. 1995, 889–896.

Bis-maleinimide

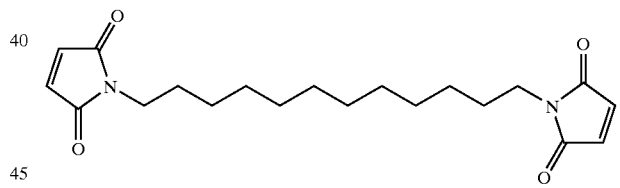

300 mg (1.49 mmol) 1,3-diaminododecane are dissolved in 10 ml CHCl3 and cooled to 0° C. N-Methoxycarbonyl maleinimide (NMM, 702 mg, 4.49 mmol) and tetrabutylammonium hydrogensulfate (508 mg, 1.49 mmol) are added. Triethylamine (0.5 ml, 3.97 mmol) is slowly added and stirring is carried out at 0° C. for another 10 min. The ice bath is removed and 20 ml saturated NaHCO3 solution are added. The reaction mixture is extracted using acetic acid ethyl ester (3×50 ml) at room temperature after 3 h. The combined organic extracts are washed once with saturated NaCl solution. The organic phase is dried with magnesium sulfate and the solvent is removed in vacuo. The desired bis-maleinimide is then purified by chromatography on silica gel (petroleum ether/EtOAc 10:1) and obtained as a colorless solid.

Yield: 420 mg (78%)

1H NMR (250 MHz, CDCl3): δ=1.25 (br.s., 16H), 1.54–1.59 (m, 4H), 3.50 (t, J=7.3 Hz, 4H), 6.68 (s, 2H).

Tris-maleinimide

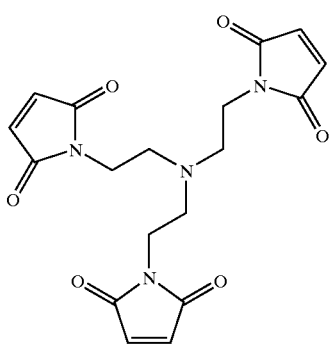

Tris-(2-aminoethyl)amine (100 mg, 0.68 mmol) is dissolved in 5 ml saturated NaHCO3 solution/THF (1:1). The solution is mixed at 0° C. portion-wise with N-(methoxycarbonyl)maleinimide (641 mg, 4.13 mmol). 20 ml saturated NaCHO3 solution/THF (1:1) are added every hour. Extraction is carried out with acetic acid ethyl ester (3×100 ml) at 0° C. after 4 h and the organic phase is washed with saturated NaCl solution (1×100 ml). The organic phase is dried with magnesium sulfate and the solvent is removed in vacuo. The desired compound is obtained as a light yellow solid.

Yield: 140 mg
1H NMR (250 MHz, CDCl3): δ=2.71 (t, J=6.6 Hz, 6H), 3.52 (t, J=6.6 Hz, 6H), 6.70 (s, 6H)
ESI-MS: [M+H+] 386.9
Synthesis of tris-maleinimide: J. C. Cheronis, E. T. Whalley, K. T. Nguyen, S. R. Eubanks, L. G. Allen, M. J. Duggan, S. D. Loy, K. A. Bonham, J. K. Blodgett, J. Med. Chem. 1992, 35, 1563–1572.

Tetra-maleinimide

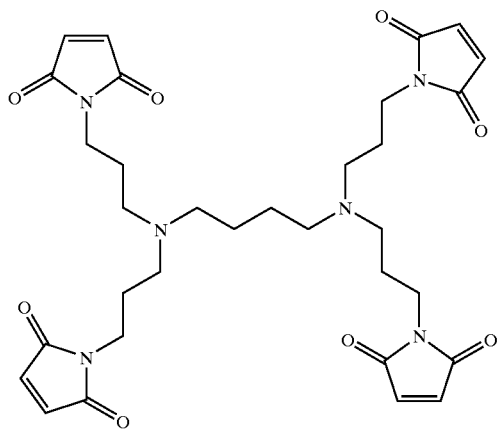

Polypropylene tetraamine dendrimer (DAB-Am-4, 90 mg, 0.28 mmol) is dissolved in 5 ml saturated NaHCO3 solution/THF (1:1). N-(methoxycarbonyl)maleinimide (356 mg, 2.27 mmol) is added portion-wise at 0° C. 20 ml saturated NaHCO3/THF solution (1:1) is added every hour. Extraction is carried out with acetic acid ethyl ester (3×100 ml) at 0° C. after 4 h, and the organic phase is washed with saturated NaCl solution (1×100 ml). The organic phase is dried with magnesium sulfate and the solvent is removed in vacuo. The desired compound is obtained as a light yellow solid.

Yield: 120 mg
1H NMR (250 MHz, CDCl3): δ=1.42–1.43 (m, 4H), 1.69 (dt, J=7.2, J=7.2 Hz, 8H), 2.37–2.40 (m, 4H), 2.40 (t, J=7.0 Hz, 8H), 3.55 (t, J=7.4 Hz, 8H), 6.68 (s, 8H).

13C NMR (63 MHz): δ=24.76, 26.16, 36.31, 51.24, 53.68, 134.04, 170.76.
ESI-MS: [M+H+] 637.2

N-maleinimido Butanoic Acid

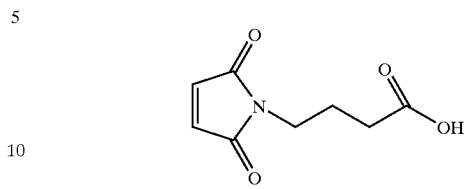

δ-Amino carboxylic acid (500 mg, 4.84 mmol) is dissolved in 20 ml saturated NaHCO3 solution/THF (1:1). N-(methoxycarbonyl)maleinimide (910 mg, 5.81 mmol) is added portion-wise at 0° C. Following 10 min. at 0° C. the temperature is raised to room temperature and 20 ml saturated NaHCO3/THF solution (1:1) are added every hour. After 3 h, extraction using acetic acid ethyl ester (3×100 ml) is carried out and the organic phase is washed with saturated NaCl solution (1×100 ml). The organic phase is dried with magnesium sulfate and the solvent is removed in vacuo. Chromatography on silica gel (EtOAc) supplies the desired compound as a colorless solid.

Yield: 798 mg (90%)

5-maleinimido Fluorescein

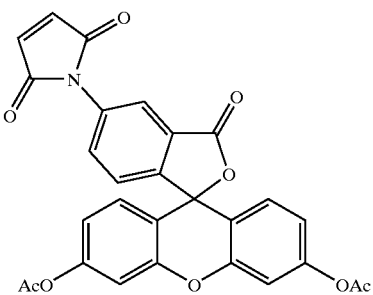

5-Aminofluorescein (500 mg, 1.44 mmol) is dissolved in 50 ml acetic acid/chloroform (1:1) (possibly suspension). Maleic acid anhydride (141 mg, 1.43 mmol) is added at room temperature and the mixture is stirred overnight. Thereafter, the solvent is removed in vacuo and the residue is taken up in acetic acid anhydride (30 ml). Sodium acetate (200 mg) is added and heated to 100° C. for 4 h. The reaction mixture is poured onto 100 ml ice water and extracted with acetic acid ethyl ester (3×100 ml). The organic phase is washed once with saturated NaCl solution and dried with magnesium sulfate. The solvent is removed in vacuo and the residue is chromatographed on silica gel (EtOAc/hexane 3:1).

Yield: 590 mg
ESI-MS: [M+H+] 512.0

N,N-bis(2-chloroethyl)-4-maleinimidoaniline

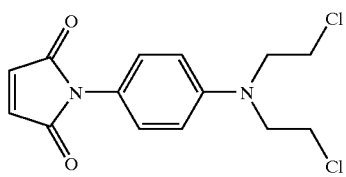

N,N-bis(2-chloroethyl)-4-nitroaniline (1.8 g, 6.87 mmol) is dissolved in methanol (40 ml) and mixed with 10% Pd/C (200 mg). The reaction mixture is stirred in an H2 atmosphere at normal pressure at room temperature for 4 h.

Thereafter, the solution is filtered and the solvent is removed in vacuo. The residue is taken up in 30 ml saturated NaHCO3/THF solution (1:1) and mixed at 0° C. portionwise with N-methoxycarbonyl maleinimide (1.61 g, 10.0 mmol). After 10 min, the ice bath is removed and stirring is carried out at room temperature for 3 h. 20 ml saturated NaHCO3/THF solution (1:1) are added every hour. The reaction mixture is extracted with acetic acid ethyl ester (3×100 ml) and the combined organic phases are washed with NaCl solution (1×100 ml). The solvent is removed in vacuo and the residue is chromatographed on silica gel with hexane/EtOAc (1:1). The desired compound is obtained as an orange solid.

Yield: 600 mg (28%)

1H NMR (250 MHz, CDCl3): δ=3.59–3.77 (m, 8H), 6.73 (d, J=9.2 Hz, 2H), 6.80 (s, 2H), 7.17 (d, J=9.2 Hz, 2H).

13C NMR (63 MHz): δ=40.24, 53.49, 112.22, 120.93, 127.84, 134.09, 145.86, 169.91.

ESI-MS: was not possible

Synthesis of N,N-bis(2-chloroethyl)-4-nitroaniline: B. D. Palmer, W. R. Wilson, S. M. Pullen, W. A. Denny, J. Med. Chem. 1990, 33, 112–121.

Synthesis of a Cis-platin Maleinimide Derivative 2,3-Diaminopropionic acid methyl ester dihydrochloride

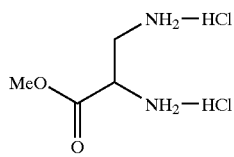

2,3-Diaminopropionic acid monohydrochloride (2.0 g, 14.3 mmol) is suspended in dry methanol (80 ml) and cooled on 0° C. Dry HCl gas is introduced into the solution for 30 min. Stirring is carried out at room temperature for 48 h, and the solvent is then removed in vacuo. The desired compound is obtained as a colorless solid and used directly for the next reaction.

Synthesis of the 2,3-diaminopropionic acid methyl ester dihydrochloride: P. Jones, G. B. Villeneuve, C. Fei, J. DeMarte, A. J. Haggarty, K. T. Nwe, D. A. Martin, A.-M. Lebuis, J. M. Finkelstein, B. J. Gour-Salin, T. H. Chan, B. R. Leyland-Jones, J. Med. Chem. 1998, 41, 3062–3077).

N,N-di-tert-butoxycarbonyl-2,3-diaminopropionic acid methyl ester

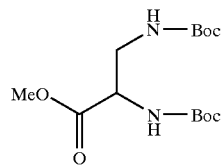

2,3-Diaminopropionic acid methyl ester dihydrochloride (1.2 g, 6.31 mmol) is dissolved in 1,4-dixan/water (40 ml, 1:1) and mixed with triethylamine (4.4 ml, 31.61 mmol). Then, di-tert-butyl dicarbonate (3.0 g, 13.78 mmol) is added and stirring is carried out overnight. Acetic acid ethyl ester (100 ml) and 1 N HCl (100 ml) are added to the reaction solution. The organic phase is washed with saturated NaCl solution (2×100) and dried using magnesium sulfate. The solvent is removed and the residue is purified by chromatography on silica gel (EtOAc/hexane 1:3). The desired compound is obtained as a colorless solid.

Yield: 1.83 g (91%)

¹H NMR (250 MHz, D6-DMSO): δ=1.36 (br. s, 18H, Boc-H), 3.20-3.25 (m, 2H), 3.59 (s, 3H, OCH3), 4.03 (t, J=7.0 Hz, CH), 6.78 (br. t, NH), 6.98 (d, J=7.6 Hz, NH).

13C NMR (63 MHz, D6-DMSO): δ=28.10, 40.97, 52.39, 61.24, 77.52, 77.58, 155.15, 155.84.

ESI-MS: [M+Na+] 341.1; [M+H+] 319.1

Method: E. B. van der Tol, H. J. van Ramesdonk, J. W. Verhoeven, F. J. Steemers, E. G. Kerver, W. Verboom, D. N. Reinhoudt, Chem. Eur. J. 1998, 4, 2315–2323.

N,N-di-tert-butoxycarbonyl-2,3-diaminopropanol

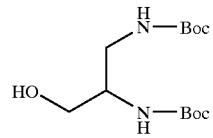

N,N-di-tert-butoxycarbonyl-2,3-diaminopropionic acid methyl ester (1.5 g, 4.70 mmol) is dissolved in dry THF (30 ml). An excess of lithium aluminum hydride (150 mg) is added portion-wise at 0° C. and stirring is carried out at room temperature for 2 h. The reaction mixture is cooled to 0° C. and hydrolyzed by adding water. Acetic acid ethyl ester (3×100 ml) is used for the extraction and saturated NaCl solution (1×100 ml) is used for washing. The organic phase is dried with magnesium sulfate and the residue is chromatographed on silica gel with hexane/EtOAc (1:1). The alcohol is obtained as a colorless solid.

Yield: 966 mg (70%)

1H NMR (250 MHz, D6-DMSO): δ=1.37 (br. s, 18H, Boc-H), 2.94–3.06 (m, 2H), 3.30 (dd, J=5.5 Hz, J=9.5 Hz, 2H), 3.40–3.46 (m, 1H, CH), 4.50 (t, J=5.6 Hz, 1H, OH), 6.23 (br. d, 1H, NH), 6.57 (br. t, 1H, NH).

13C NMR (63 MHz, D6-DMSO): δ=28.10, 40.97, 52.39, 61.24, 77.52, 77.58, 155.15, 155.84.

ESI-MS: [M+Na+] 312.9; [M+H+] 290.9

N,N-di-tert-butoxycarbonyl-2,3-diaminopropyl maleinimide

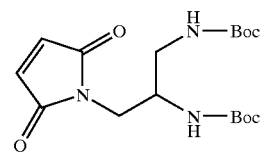

N,N-di-tert-butoxycarbonyl-2,3-diaminopropanol (400 mg, 1.38 mmol) is dissolved in dry THF and mixed with triphenylphosphine (398 mg, 1.52 mmol) and maleinimide (148 mg, 1.52 mmol). Then, DEAD (0.26 ml, 1.67 mol) is added dropwise and stirring is carried out at room temperature for 24 h. The solvent is removed in vacuo and the residue is chromatographed twice on silica gel with hexane/EtOAc 2:1. The desired compound is obtained as a colorless solid but not in pure form. Separation by means of HPLC did not yield the desired success either.

Yield: 50 mg

ESI-MS: [2M+Na+] 761.2; [M+Na+] 392.0; [M+H+] 370.1

1H NMR (250 MHz, CDCl3): δ=1.39 (br. s, 9H, Boc-H), 1.44 (br. s, 9H, Boc-H), 3.22 (t, J=5.9 Hz, 2H), 3.61 (d, J=6.6 Hz, 2H), 3.80–3.88 (m, 1H), 5.00–5.15 (m, 2H, NH), 6.72 (s, 2H)

Mitsunobu reactions with maleinimide:

M. A. Walker, Tetrahedron Lett. 1994, 35, 665–668.

M. A. Walker, J. Org. Chem. 1995, 60, 5352–5355.

M. A. Walker, Tetrahedron 1997, 53, 14591–14598.

K. I. Booker-Milburn, C. E. Anson, C. Clissold, N. J. Costin, R. F. Dainty, M. Murray, D. Patel, A. Sharpe, Eur. J. Org. Chem. 2001, 1473–1482.

Mitsunobu reactions with scavenger reagents:

L. D. Arnold, H. I. Assil, J. C. Verderas, J. Am. Chem. Soc. 1989, 111, 3973–3976.

Commercially available maleinimide derivatives which were used successfully in the Diels-Alder reaction:

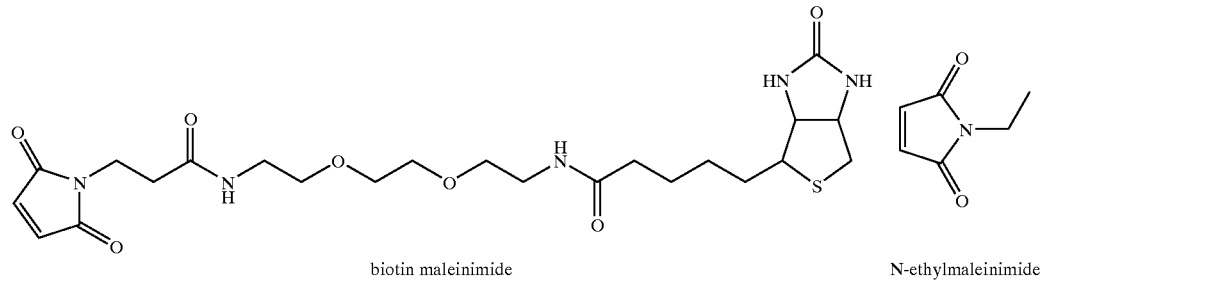

biotin maleinimide

N-ethylmaleinimide

EXAMPLE 10

Diels-Alder Reactions

All of the compounds shown were prepared according to the general instruction and purified by means of HPLC. They were characterized at least by ESI mass spectra, often in addition by NMR ($^1$H— and $^{13}$C).

General Instruction:

The furan derivative is dissolved with the corresponding maleinimide derivative in water or, if necessary, in a mixture of THF/water (5:2) and stirred several (2–4) days at 50° C. Thereafter, the solvent is removed in vacuo and the residue is purified on silica gel (CH2Cl2/MeOH 5:1). The corresponding Diels-Alder adducts were obtained as mixtures of exo/endo and could partly be separated.

Synthesized Diels-Alder Products with N-ethylmaleinimide as Dienophile:

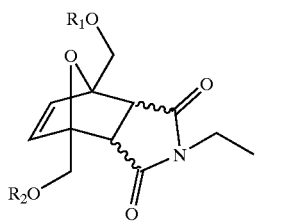

$R_1/R_2$: fucose/fucose, galactose/galactose and fucose/galactose

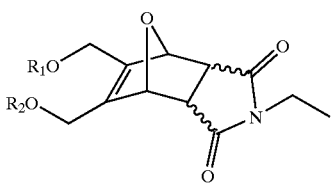

$R_1/R_2$: H/H: H/galactose; H/fucose; fucose/fucose, galactose/galactose and fucose/galactose, lactose/lactose

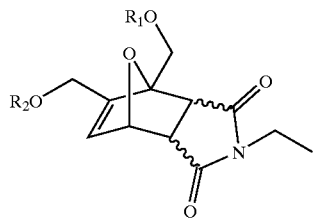

$R_1/R_2$: fucose/fucose, galactose/galactose

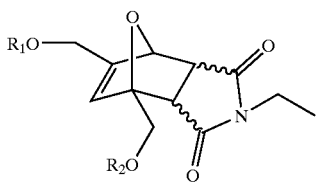

$R_1/R_2$: fucose/fucose, galactose/galactose

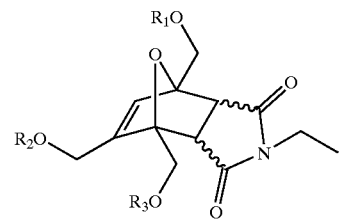

$R_1/R_2/R_3$: fucose/fucose/fucose

Synthesized Diels-Alder Products with Biotin Maleinimide as Dienophile:

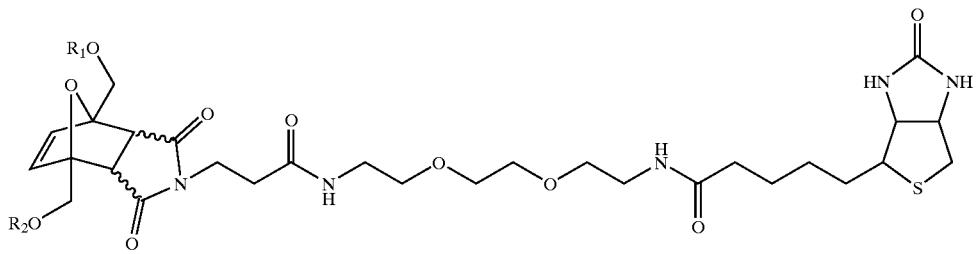

R₁/R₂: fucose/fucose, galactose/galactose and fucose/galactose

Compound with biotin maleinimide are particularly suited for clarifying cellular surface structures and therefore for the diagnosis and therapy.

Other synthesized Diels-Alder Products:

acrylamide as dienophile

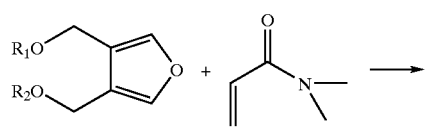

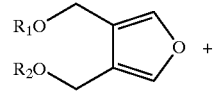

R₁/R₂: fucose/fucose

Introduction of Carborane-derivatized Furan and N-ethylmaleinimide

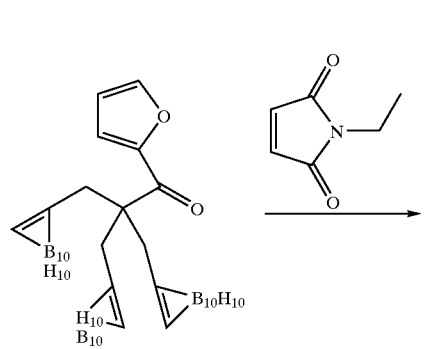

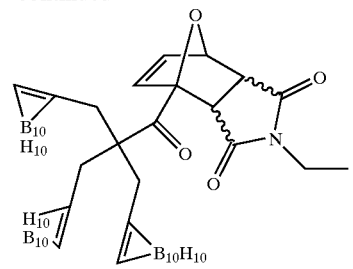

Diels-Alder Reaction with Nucleosides (as an Example of Diels-Alder Reaction on Oligonucleotides, DNA)

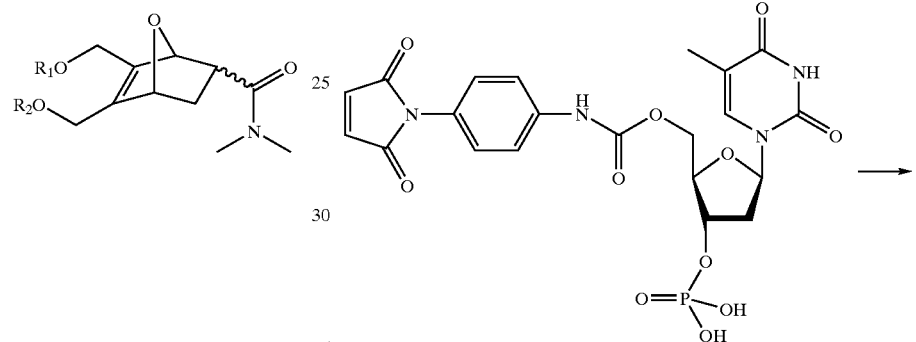

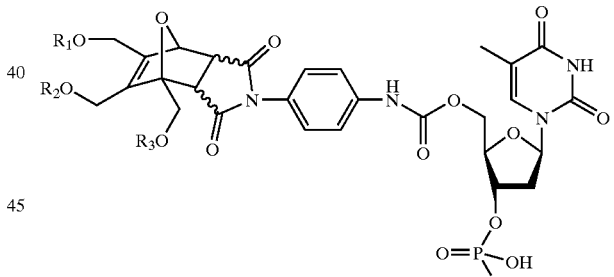

Trimethoxyphenylmaleinimide (Potential Active Substances, P53)

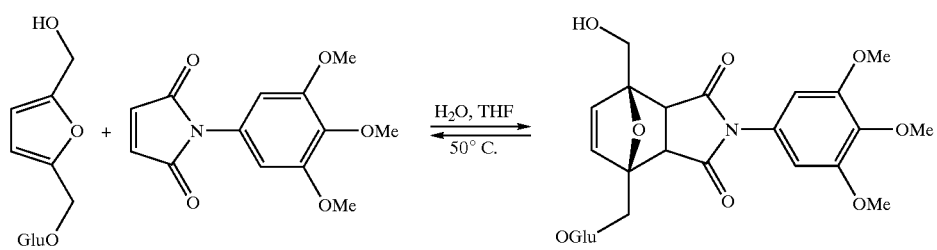

Bromophenylmaleinimide (Potential Active Substances, P53)

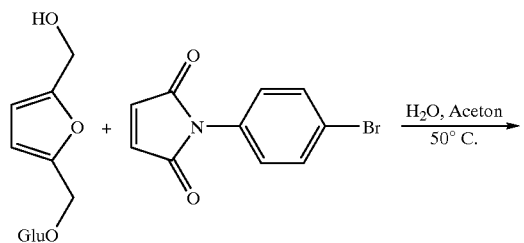

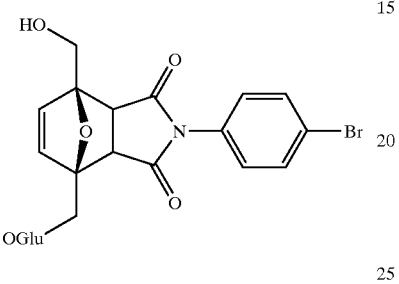

This reaction was also carried successfully out with 3,4- and 2,5-bishydroxymethyl furans fucosylated or galactosylated twice.

In both above compounds a combinatorial approach was made. For example, relatively small libraries of novel, potential medicaments, e.g. as modulators of/for p53, can be produced by combining differently glycosylated furans.

Diels-Alder Product with Maleic Acid Anhydride

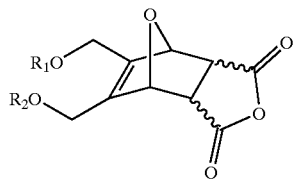

$R_1/R_2$. fucose/fucose
and a derivative thereof:

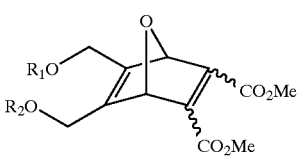

In the following four reactions, the 2-glucosylmethyl-5-hydroxymethyl furan was used as a furan derivative.
with cholesterol:

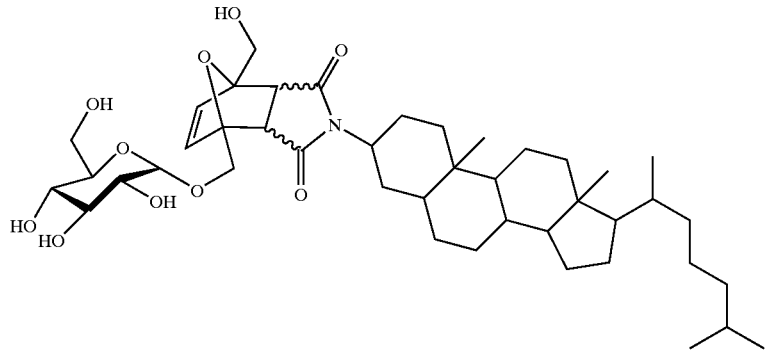

Batch: 240 mg (0.82 mmol) furan
530 mg (1.13 mmol) N-cholesteryl maleinimide
Yield: 250 mg (44%)
ESI-MS: [M+Cl−] 792.7

Dodecane (Lipophilic Residue)

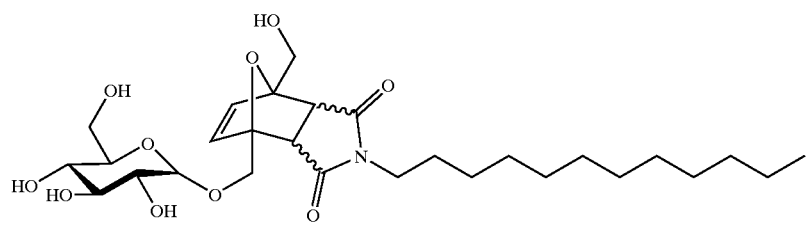

Batch: 200 mg (0.69 mmol) furan
365 mg (1.38 mmol) N-dodecyl maleinimide
Yield: 210 mg (55%)
ESI-MS: [M+Na+] 578.0
Steryl Residue (Lipophilic Residue)

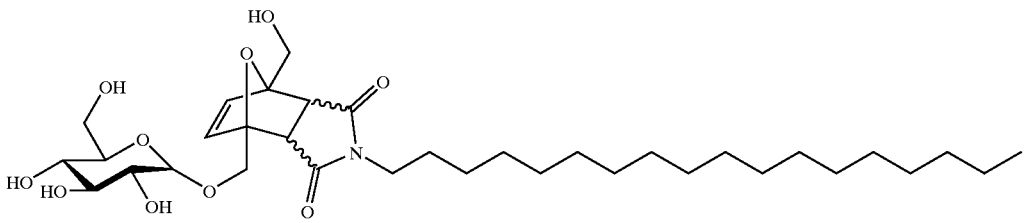

Batch: 200 mg (0.69 mmol) furan
300 mg (0.86 mmol) N-stearyl maleinimide
Yield: 230 mg (52%)
ESI-MS: [M+Cl−] 674.5
Aniline Lost (Analogous Glu-IPM)

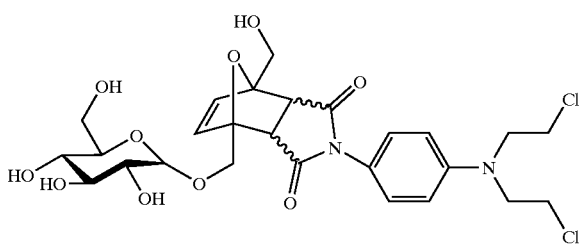

Batch: 100 mg (0.34 mmol) furan
215 mg (0.68 mmol) aniline-N-lost maleinimide
Yield: <50 mg
ESI-MS: [M+Na+] 625.0

EXAMPLE 11

Diels-Alder Reaction with an Amino Acid (Lysine)

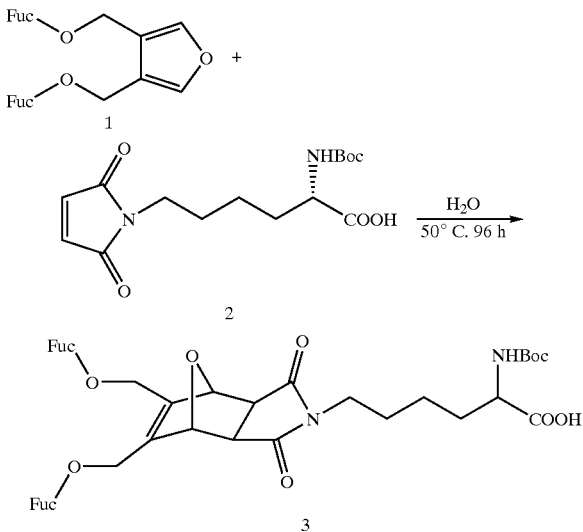

2-tert-butoxycarbonylamino-6-[3,5-dioxo-8,9-bis-(3,4,5trihydroxy-6-methyl-tetrahydro-pyran-2-yloxymethyl)-10-oxa-4-aza-tricyclo[5.2.1.02,6]dec-4-yl]hexanoic acid (3): 0.033 g (0.1 mmol) 2 (prepared according to the instruction of [1]) are added to a solution of 0.042 g (0.1 mmol 1 in 3 ml water adjusted to a pH of 6.9 and then stirred at 50° C. for 4 days. The solvent is removed by freeze drying and the white crude product (0.075 g) is purified by means of preparative HPLC.

12 mg and 16 mg of two conformers are obtained. Total yield 40%. ESI-MS: 647.2 [(MH-Boc]+H]+, 669.1 [(MH-Boc)+Na]+, 769.2 [M+Na]+, 1293.3 [2(MH-Bov)+H]+, 1315.4 [2(MH-Boc)+Na]+

HPLC: Abimed.:
Analytical: Merck Lichrospher-RP18(E) 5μ, (250×4) mm, water: CH3CN (100:0)% degree 40 min 100% CH3CN, 1 ml/min flow, detection at 210 nm
preparative: Merck Lichrospher-RP18(E) 5μ, (250×25) mm, water: CH3CN (100:0)% degree 45 min. 25% CH3CN, 10 ml/min flow, detection at 210 nm

What is claimed is:

1. A method for synthesizing a saccharide compound comprising the steps of:
reacting a saccharide-containing cyclic diene with a dienophile by Diels-Alder reaction.

2. The method according to claim 1, wherein the cyclic diene is a substituted furan, fulvene, furfural, pyrrole, pyrazole, oxazole, thiophene, cyclopentadiene or cyclohexadiene.

3. The method according to claim 2, wherein the cyclic diene has one or more substituents selected from the group consisting of alkyl, OH, SH, halogen, amino, aryl, carboxyl, nitro, carboxyamido, keto, sulfoxide, sulfone, sulfonic acid, phosphoric acid, amino acid, peptide, oligonucleotide, nucleic acid, lipid, and saccharide.

4. The method according to claim 1, wherein the dienophile is an enol ether derivative, a maleic acid derivative, a fumaric acid derivative, a maleinimide derivative, an acrylic acid derivative, or an acetylene derivative, wherein said derivative has one or more substituents selected from the group consisting of alkyl, OH, SH, halogen, amino, aryl, carboxy, carbonyl, nitro, carboxyamido, keto, sulfoxide, sulfone, sulfonic acid, phosphoric acid, phosphonic acid, mono-, di- or trialkylamide, amino acid, oligonucleotide, nucleic acid, lipid and saccharide.

5. The method according to claim 4, wherein said maleic acid derivative is a maleic acid anhydride and said fumaric acid derivative is a fumaric acid anhydride.

6. The method according to claim 1, wherein the cyclic diene has one or more substituents selected from the group consisting of alkyl, OH, SH, amino, halogens, aryl, carboxyl, nitro, carboxyamido, keto, sulfoxide, sulfone, sulfonic acid, phosphoric acid, amino acid, biotin, peptides, oligonucleotide, nucleic acid, lipid, and saccharide.

7. The method according to claim 6, wherein the substituent is a lysine residue.

8. The method according to claim 1, wherein the saccharide-containing cyclic diene is prepared by substituting a saccharide with an imidate component at position 1 of the saccharide hemiacetal and reacting a cyclic diene with the imidate component.

9. The method according to claim 8, wherein the imidate substituted saccharide is tri-O-benzoylfucose imidate or tetra-O-benzoyl galactose imidate.

10. The method according to claim 1, wherein the cyclic diene is selected from the group consisting of 2,3-bishydroxymethyl furan, 3,4-bishydroxymethyl furan, 2,5-bishydroxymethyl furan, and a 5-glucosylmethyl furfural with modified aldehyde function.

11. The method according to claim 1, wherein the saccharide-containing cyclic diene is 3,4-bis(fucosyloxymethyl)furan, 3,4-bis-(galactosyloxymethyl)-furan, 3-galactosyl hydroxymethyl-4-fucosyl hydroxymethyl furan, 3-fucosyl-4-fucosyl-3,4-bis-hydroxymethyl furan, 3-fucosyl-4-galactosyl-3,4-bis-hydroxymethyl furan, 2-galactosyl-5-galactosyl-2,5-bis hydroxymethyl furan or 2,5-bis-(galactosyl oxymethyl) furan.

12. The method according to claim 1, wherein the reaction is repeated.

13. A method of synthesizing a saccharide compound comprising the steps of:

reacting a saccharide-containing furan with a dienophile by Diels-Alder reaction.

14. The method according to claim 13, wherein the furan contains a hydroxy group.

15. The method according to claim 13, wherein the furan has one or more substituents selected from the group consisting of alkyl, OH, SH, halogen, amino, aryl, carboxyl, nitro, carboxyamido, keto, sulfoxide, sulfone, sulfonic acid, phosphoric acid, amino acid, biotin, peptide, oligonucleotide, nucleic acid, lipid, and saccharide.

16. The method according to claim 15, wherein the substituent is a lysine residue.

17. The method according to claim 13, wherein the dienophile is an enol ether or a maleic acid derivative, fumaric acid derivative, maleinimide derivative, acrylic acid derivative, acetylene derivative, wherein said derivative has one or more substituents selected from the group consisting of alkyl, OH, SH, halogen, amino, aryl, carboxy, carbonyl, nitro, carboxyamido, keto, sulfoxide, sulfone, sulfonic acid, phosphoric acid, phosphonic acid, mono-, di- or trialkylamide, amino acid, peptide, oligonucleotide, nucleic acid, lipid and saccharide.

18. The method according to claim 17, wherein said maleic acid derivative is a maleic acid anhydride and said fumaric acid derivative is a fumaric acid anhydride.

19. The method according to claim 13, wherein the saccharide-containing furan is prepared by substituting a saccharide with an imidate component at position 1 of the saccharide hemiacetal and reacting a furan with the imidate component.

20. The method according to claim 19, wherein the saccharide substituted with an imidate is tri-O-benoylfucose imidate or tetra-O-benzoyl galactose imidate.

21. The method according to claim 13, wherein the furan is selected from the group consisting of 2,3-bishydroxymethyl furan, 3,4-bishydroxymethyl furan, 2,5-bishydroxymethyl furan, and a 5-glucosylmethyl furfural with a modified aldehyde function.

22. The method according to claim 13, wherein the saccharide-containing furan is 3,4-bis(fucosyloxymethyl) furan, 3,4-bis-(galactosyloxymethyl)-furan, 3-galactosyl hydroxymethyl-4-fucosyl hydroxymethyl furan, 3-fucosyl-4-fucosyl-3,4-bis-hydroxymethyl furan, or 2,5-bis-(galactosyl oxymethyl) furan.

23. The method according to claim 13, wherein the reaction is repeated.

* * * * *